US008268338B2

(12) United States Patent
Texter

(10) Patent No.: US 8,268,338 B2
(45) Date of Patent: Sep. 18, 2012

(54) BACTERICIDAL SILVER SURFACTANT DELIVERY INTO COATING AND POLYMER COMPOSITIONS

(75) Inventor: John Texter, Ypsilanti, MI (US)

(73) Assignee: Eastern Michigan University, Ypsilanti, MI (US)

( * ) Notice: Subject to any disclaimer, the term of this patent is extended or adjusted under 35 U.S.C. 154(b) by 1031 days.

(21) Appl. No.: 12/170,397

(22) Filed: Jul. 9, 2008

(65) Prior Publication Data

US 2009/0018188 A1 Jan. 15, 2009

Related U.S. Application Data

(60) Provisional application No. 60/958,836, filed on Jul. 9, 2007.

(51) Int. Cl.
*A01N 25/00* (2006.01)
(52) U.S. Cl. .......................................... 424/405; 423/45
(58) Field of Classification Search .................. None
See application file for complete search history.

(56) References Cited

U.S. PATENT DOCUMENTS

| 4,297,100 A * | 10/1981 | Koci et al. .................. 8/527 |
| 6,660,058 B1 * | 12/2003 | Oh et al. .................. 75/351 |
| 7,261,867 B1 * | 8/2007 | Sandford et al. ........... 423/45 |
| 2004/0057909 A1 * | 3/2004 | Moszner et al. ........... 424/49 |
| 2005/0249791 A1 * | 11/2005 | Hobbs et al. ............. 424/443 |
| 2006/0141015 A1 * | 6/2006 | Tessier et al. ............ 424/443 |
| 2009/0013825 A1 * | 1/2009 | Rahman Nia ............. 75/343 |

FOREIGN PATENT DOCUMENTS

| JP | 03-141205 | * | 6/1991 |
| JP | 2001-029451 | * | 2/2001 |

OTHER PUBLICATIONS

Texter et al "Bactericidal silver ion delivery into hydrophobic coatings with surfactants"; J Ind Microbiol Biotechnol (2007) 34:571-575 (published online Jun. 19, 2007).*
Machine Translation of JP 2001-029451A pp. 1-9; retrieved on Sep. 9, 2011.*
English Abstract of JP 03-141205 from the Japanese Patent website; retrieved on Sep. 9, 2011 (p. 1).*
English Translation of JP 03-141205 (published on Jun. 1991) pp. 1-17.*
Nobuyoshi Akimitsu et al., Antimicrobial Agents and Chemotherapy, Dec. 1999, p. 3042-3043.
Ritu Bansal-Mutalik and Vilas G. Gaikar, 2003, Enzyme and Microbial Technology 32: 14-26.
Szczepan Zapotoczny, Monika Golonka, and Maria Nowakowska, Langmuir 2008, 24, 5868-5876.
Byun et al., J. appl. Polym. Sci. 2000, 76, 787-798.
Morgan et al., Langmuir 2007, 23, 230-240.
Sumerlin, B.S.; Lowe, A.B.; Thomas, D.B.; McCormick, C. L. Macromolecules 2003, 36, 5982-5987.
Eastoe et al., Langmuir 1993, 9, 2920-2824.
Sandrine Nave, Julian Eastoe, Jeff Penfold, Langmuir 2000, 16, 8733-8740.
Dickson et al., Ind. Eng. Chem. Res. 2005, 44, 1370-1380.
Francesca Baldelli Bombelli, Debora Berti, Uwe Keiderling, Piero Baglioni, J. Phys. Chem. B 2002, 106, 11613-11621.
A.K. Chattopadhyay, D.O. Shah, L. Ghaichao, Langmuir 1992, 8, 27-30.
Laurent Wattebled and André Laschewsky, Colloid Polym. Sci., 2007, 285:1387-1393.
S.K. Hait and S.P. Moulik, Current Science, vol. 82, No. 9, May 10, 2002, pp. 1101-1111.
Menger and Littau, J. Am. Chem. Soc, 1991, 113, 1451-1452.
Jaeger, D.J. and Brown, E.L.G., Langmuir, 1996, 12, 1976-1980.
S. Jason Keiper et al., Langmuir 2004, 20, 1065-1072.
Petit et al., 1993, J. Phys. Chem. 97: 12974-12983.
Steytler et al., Langmuir 1996, 12, 1483-1489.
Eastoe et al., J. Phys. Chem. 1993, 97, 1459-1463.
Texter et al., 2004, Macromolecules 37: 5841-5843.
Texter et al., 2005 Macromolecules Correction 37: 7424.
W. Chen, J.A. Sauer, M. Hara, Polymer 45, 2004, 7219-7227.

* cited by examiner

*Primary Examiner* — Bethany Barham
(74) *Attorney, Agent, or Firm* — Dickinson Wright PLLC

(57) ABSTRACT

Disclosed are surfactant compounds and compositions that are antimicrobial. Also provided are polymeric compositions incorporating the surfactant compounds. The polymeric compositions may be used to form antibacterial coatings on surfaces.

20 Claims, No Drawings

BACTERICIDAL SILVER SURFACTANT DELIVERY INTO COATING AND POLYMER COMPOSITIONS

CROSS REFERENCE TO RELATED APPLICATIONS

This application claims priority to U.S. Provisional Application Ser. No. 60/958,836, filed Jul. 9, 2007, which is hereby incorporated by reference.

STATEMENT REGARDING FEDERALLY SPONSORED RESEARCH

This invention was made with U.S. Government support under Grant No. DAAE07-03-C-L127 awarded in part by the United States Army Tank-automotive and Armaments Command (TACOM). The government has certain rights in the invention.

TECHNICAL FIELD

The invention relates generally to surfactants, more particularly, to anionic surfactants, and to anionic polyelectrolytes. More particularly, this invention relates to anionic surfactants and anionic polyelectrolytes that are monodentate ligands for cations such as silver or sodium ions. This invention further relates to anionic surfactants that form reverse micelles and reverse microemulsions.

INTRODUCTION

Antimicrobial compositions are used in the health care industry, food service industry, meat processing industry, and, of course, by individual consumers. Such widespread use of these compositions is indicative of the importance placed on controlling bacteria and other microorganism populations.

In general, antimicrobial agents are directed at bacteria, viruses, and fungi. Most agents, however, generally have a limited spectrum of activity. For example, bactericidal agents typically are not fungicidal, while fungicidal agents typically are not bactericidal. Quaternary surfactants and agents have known antimicrobial properties. However, many irritate human skin and are unsuitable for many antimicrobial formulations. Anionic surfactants, although useful for washing or soap formulations, are considered, with a few exceptions, to lack antimicrobial activity.

The need for new disinfectant compositions is increasing in view of the development of methicillin resistant *Staphylococcus aureus* (MRSA). The need for new disinfectant compositions is increasing in view of the development of benzalkonium chloride resistant organisms (Nobuyoshi Akimitsu et al., *Antimicrobial Agents and Chemotherapy*, December 1999, p. 3042-3043).

Ritu Bansal-Mutalik and Vilas G. Gaikar reported effects of reverse micelles on extractions from *Escherichia coli* ((2003) *Enzyme and Microbial Technology* 32: 14-26). Water-in-hexane macro- and micro-emulsions stabilized by sodium bis-(2-ethylhexyl)sulfosuccinate (NaAOT) were used for selective permeabilization of *E. coli* cells to extract penicillin acylase (3.5.1.11). Various organic solvents and surfactants were compared for the yield and purification of the enzyme. Recoveries up to 144% with respect to sonication and specific activity of the enzyme up to 26 units/mg have been achieved. Due to low solubilities of NaAOT and aliphatic hydrocarbons in water, the recovered enzyme was free from contaminants. A possible mechanism for cell permeabilization and enzyme purification by reverse micellar treatment was proposed.

SUMMARY

In accordance with the invention, provided are antimicrobial compositions or coating compositions comprising an anionic surfactant or an anionic polyelectrolyte. The invention further provides antimicrobial polymeric compositions.

In another embodiment, the invention provides a method of making an antibacterial polymer coating.

In yet another embodiment, the invention provides an article of manufacture comprising an anionic surfactant or an anionic polyelectrolyte.

In a further embodiment, the invention provides a method of treating an infection or burn comprising administration of a composition comprising an anionic surfactant or an anionic polyelectrolyte.

Other aspects of the invention will become apparent by consideration of the detailed description and accompanying drawings.

DETAILED DESCRIPTION

In accordance with the invention, anionic surfactants and anionic polyelectrolytes are provided for delivering cations such as silver ion ($Ag^+$) into various compositions. The invention further provides compositions including anionic surfactants or anionic polyelectrolytes and silver ion compositions that have antimicrobial properties. It has surprisingly been discovered that anionic surfactants and suitable anionic polyelectrolytes of the invention serve as monodentate ligands for ions such as $Ag^+$ and facilitate the incorporation of the ions into nonaqueous compositions to render the compositions antimicrobial, specifically, bactericidal.

In accordance with the invention, a class of anionic surfactants has been discovered that is lethal to Gram positive bacteria.

For the following defined terms, these definitions shall be applied, unless a different definition is given in the claims or elsewhere in this specification.

All numeric values herein are assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, % by weight, wt %, and the like are synonyms that refer to the concentration of a substance as the weight of that substance divided by the weight of the composition and multiplied by 100.

As used in the specification and the appended claims, the singular forms "a," "an," and "the" include plural referents unless the content clearly dictates otherwise. Thus, for example, reference to a composition containing "a compound" includes a mixture of two more compounds. As used in this specification and the appended claims, the term "or" is generally employed in its sense including "and/or" unless the content clearly dictates otherwise.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

It is further understood that the invention is not limited in its application to the details of preparation and arrangement of components set forth in the following description or illustrated in the following examples. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. "Comprising" encompasses the terms "consisting of" and "consisting essentially of." The use of "consisting essentially of" means that a composition or method may include additional ingredients or steps, but only if the additional ingredients or steps do not materially alter the basic and novel characteristics of the claimed composition or method.

Anionic Surfactants and Anionic Polyelectrolytes

Compounds embodying the principles of the invention include anionic surfactants and anionic polyelectrolytes. Such surfactants and polyelectrolytes serve as monodentate ligands for silver ion and other metal ions, such as sodium, and serve as vectors or sequestering agents to carry silver ion into suitable solutions, often nonaqueous and hydrophobic solutions. A monodentate ligand is a ligand that forms only one bond with the central atom, which is usually a metal ion. The type and structure chosen for the anionic surfactants and anionic polyelectrolytes depends on the solvent chosen and the final molecular composition into which the silver ion is to be sequestered and in which the silver ion is to exhibit its antimicrobial activity. For example, if the final composition has a significant poly(ethylene oxide) content, surfactants such as alkyloligomericethyleoxidesulfates may be particularly useful for incorporating silver ion. Many of the anionic surfactants of the present invention are commercially available. Anionic surfactants for particular applications may be easily prepared by chemical procedures well known in the art and by methods described herein.

Anionic surfactants are amphiphilic ions that typically have a hydrophobic or solvophobic part (for example, a dodecyl hydrocarbon tail as a hydrophobic group) and a hydrophilic or solvophilic part (for example, a sulfate group bearing a negative charge, and a counter ion such as any alkali metal ion, such as $Na^+$, or some small ammonium ion or the like). The surfactant is termed "anionic" because its anionic component is amphiphilic and will tend to segregate to interfaces, such as air/liquid, air/solid, and liquid/liquid interfaces. For example, at an oil/water interface, the dodecyl group would mostly solubilize on the oil side of the interface, and the sulfate group would locate on the water side of the interface, along with the counter cation.

The syntheses of surfactants such as soaps, ether carboxylic acids, alkylarylsulfonates, alkane sulfonates, olefin sulfonates, alcohol sulfates, alcohol ether sulfates, sulfated glycerides, sulfated alkanol amides, isethionates, taurates, sarcosinates, N-acyl amino acids, and α-sulfo fatty acid methyl esters are well known in the art. The syntheses of most of these surfactants are described in *Reactions and Synthesis in Surfactant Systems* edited by John Texter (Marcel Dekker, New York, 2001) in Chapter 1 (Ansgar Behler et al., pp. 1-44).

Specially, soaps are obtained by saponification of triglycerides in the presence of the desired alkali hydroxide (e.g., NaOH), by saponification of fatty acid obtained from fats and oils, and by saponification of fatty acid methyl esters derived from fats and oils.

Ether carboxylic acids are obtained from fatty alcohol ethoxylates by reaction with chloroacetic acid in the presence of NaOH, by terminal oxidation of the fatty acid ethoxylate over Pt/C and neutralization with NaOH, and by the addition of a vinylic system, such as acrylonitrile, which hydrolyzes in aqueous HCl to the carboxylic acid, which is then neutralized with the desired metal hydroxide.

Alkylarylsulfonates are obtained by reacting an alkylaryl, such as a linear or branched alkylbenzene, with oleum, sulfuric acid, or gaseous sulfur trioxide, and after aging are neutralized with NaOH or other alkali hydroxide.

Alkane sulfonates are obtained by contacting an alkane-water mixture with sulfur dioxide gas and oxygen at 30-40° C. under UV irradiation by sulfoxidation to produce the alkyl radical (R.), that then produces $RSO_2$·, and after coupling with oxygen $RSO_2OO$·, and "chain transfer" with the starting material, RH, $RSO_2OOH$, with the generation of R. to keep the synthesis going. The $RSO_2OOH$ then reacts with water and sulfur dioxide to give $RSO_3H$ and sulfuric acid.

Olefin sulfonates, especially α-olefin sulfonates (AOS), are obtained by reacting the alkene with $SO_3$ to produce the sultone. The sultone abstracts a hydrogen atom from the carbon adjacent to the sultone (to the original double bond) carbon to which the oxygen added to yield the alkenyl sulfonate. Hydrolysis converts any minor sultones of larger ring size to the corresponding γ-hydroxy (and higher) alkane sulfonic acids. Neutralization with the desired hydroxide (e.g., NaOH) yields the olefin sulfonate.

α-Sulfo fatty acid methyl esters are obtained from fatty acid methyl esters reacted with a 20% excess of $SO_3$ in air. The $SO_3$ initially inserts into the ester linkage but ends up inserted on the alpha carbon to produce the sulfonic acid. Neutralization with NaOH produces the α-sulfo fatty acid methyl ester.

Alcohol sulfates and alcohol ether sulfates are obtained by reacting the alcohol (X—OH) with 2 equivalents of sulfur trioxide gas to obtain the pryosulfate, X—$OSO_2OSO_3H$. The pyrosulfate then reacts with another alcohol, X—OH, to give two equivalents of the desired sulfate. Neutralization with alkali produces the desired salt.

Sulfated glycerides are obtained by reacting glycerol with oleum to obtain glycerol trifulfuric acid half-ester. Two moles of this half-ester are reacted with one of a triglyceride, and through a type of transesterification one obtains 3 moles of monoglyceride sulfuric acid half-ester and three moles of sulfuric acid. Neutralization with alkali yields the sulfate glyceride.

Sulfated alkanol amides are obtained by reacting the alcohol amide (X—OH) with 2 equivalents of sulfur trioxide gas to obtain the pyrosulfate, X—$OSO_2OSO_3H$. The pyrosulfate then reacts with another alcohol amide, X—OH, to give two equivalents of the desired sulfate. Neutralization with alkali produces the desired salt. Amide ether sulfates are obtained similarly if the amide ethoxylate is available. Otherwise an alkanol amide is ethoxylated and then reacted with sulfur trioxide.

Isethionates are obtained by condensation of a fatty acid or other carboxylate with sodium isethionate in the presence of an esterification catalyst at 200° C. or above. Alternatively, an acid chloride is reacted with sodium isethionate to good yield after the HCl by product is removed.

Taurates are similarly condensed with fatty acid chlorides or other carboxylate chlorides to yield the taurate and the HCl by product. The carboxylic forms may be reacted directly at high temperature under esterification (amidation) conditions with water as the byproduct from condensation with the secondary amine.

Sarcosinates are most readily obtained by condensing the sodium form of sarcosinic acid with fatty acid chlorides or with other acid chlorides, followed by removal of the HCl produced.

N-acyl amino acids can similarly be obtained by condensing the desired acid chloride with the sodium form of the amino acid after removal of the HCl.

Phosphoric acid monoesters are obtained by reacting polyphosphoric acid with 3 equivalents of alcohol, ROH, to obtain 3 equivalents of the monoester and 3 equivalents of phosphoric acid. Phosphorous pentoxide ($P_4O_{10}$) when reacted with 3 equivalents of water produces polyphosphoric acid, $H_6P_4O_{13}$. The monoesters are also obtained in 33% yield when phosphorous pentaoxide is reacted with 6 moles of ROH. Here 4 moles of diester are obtained as the predominant product.

Polyelectrolytes that incorporate monodentate ligands for ions such as silver ions include carboxylates, sulfates, sulfonates, and phosphates and are useful anionic polyelectrolytes of the present invention. Polystyrenesulfonate and copolymers of styrene sulfonate may suitably incorporate silver ion into solutions and compositions of the present invention. Selection of co-monomers can be made so as to make the silver exchanged copolymer compatible with the final polymeric or coating composition. Poly(sodium 4-styrenesulfonate) (PSS, $M_w$=70,000 g mol$^{-1}$) is available from Sigma-Aldrich (St. Louis, Mo., U.S.A). Similarly polyvinylsulfate and copolymers of vinylsulfate are anionic polyelectrolytes of the present invention. Poly(potassium vinyl sulfate) (PVS, $(C_2H_3KO_4S)$ 162.1)$_n$, n>1500), can be obtained from Wako Pure Chemical Industries, Ltd. (Osaka, Japan).

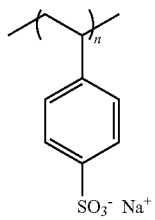
PSS

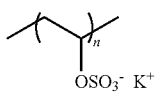
PVS

Varying co-monomer to achieve desired comparability and performance properties is well understood in the art. A statistical copolymer (Szczepan Zapotoczny, Monika Golonka, and Maria Nowakowska. *Langmuir* 2008, 24, 5868-5876) of sodium p-styrenesulfonate (SSS) and 2-vinylnaphthalene (VN) of molecular weight 150,000 g/mol is synthesized using the free-radical polymerization of the appropriate mixture of the monomers in degassed dimethyl sulfoxide (DMSO) solution for 21 h at 60° C. using 2,2'-azobis(2-methylpropionitrile) (AIBN, 0.1 mol %) as an initiator. The content of VN monomer in the reaction mixtures is set to 50 mol %, and the composition of the resulting copolymer is found using $^1$H NMR spectroscopy and elemental analysis to be almost the same (48 mol %) as the feed ratio. The resulting copolymer is purified by dialysis (Fisher, cellulose tubing, cutoff 12,000-14,000 g/mol; from Fisher Scientific, Waltham, Mass., U.S.A.) and subsequently freeze-dried.

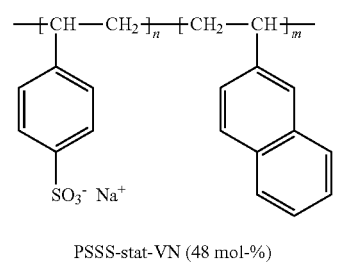
PSSS-stat-VN (48 mol-%)

Additionally polyacrylate (PA) and polymethacrylate are excellent homopolymers for complexing with ions such as silver ion and for carrying them into various substrates and compositions of the present invention. The natural product, i-type Carrageenan (CAG), is available from Sigma-Aldrich (St. Louis, Mo., U.S.A.) as the sodium salt.

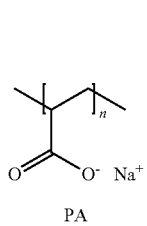
PA

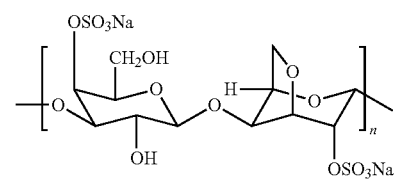
CAG

Water insoluble sulfonated poly(sulfone) sodium salts (SPSF) with different ionic exchange capacities (IEC) and weight average molecular weights (MW) (IEC/MW) 0.85/94,000 g/mol and 0.65/83,000 g/mol) may be sulfonated by an $SO_3$-TEP complex (2:1) by a method according to Byun et al. (*J. Appl. Polym. Sci.* 2000, 76, 787.).

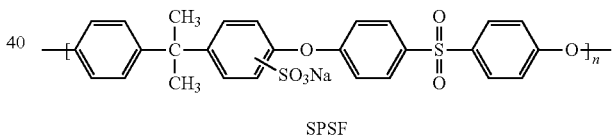
SPSF

Dextran sodium sulfate (DxS) is available commercially from Sigma-Aldrich (St. Louis, Mo., U.S.A.).

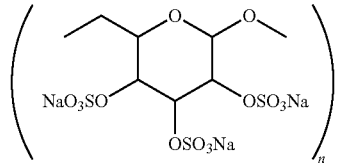
DxS

Structures (Morgan et al., *Langmuir* 2007, 23, 230-240) of anionic polymers (SA) poly(sodium 2-acrylamido-2-methylpropane sulfonate) P(AMPS), (WA) poly(sodium 3-acrylamido-3-methylbutonate) P(AMBA), (B) poly(sodium 3-acrylamido-3-methylbutonate-b-sodium-2-acrylamido-2-methylpropane sulfonate) P(AMBA-b-AMPS), (R) poly-(sodium 3-acrylamido-3-methylbutonate-r-sodium-2-acrylamido-2-methylpropanesulfonate) P(AMBA-r-AMPS), homo and block copolymers of AMPS and AMBA are prepared using a method similar to that reported (Sumerlin, B. S.; Lowe, A. B.; Thomas, D. B.; McCormick, C. L. *Macromolecules* 2003, 36, 5982-5987.). Briefly, homopolymers of AMPS and AMBA were prepared in water at 70° C. with V-501 as the initiator and CTP as the RAFT chain-transfer agent. The [CTA]/[V-501] ratio may be a 5:1 mole basis, with [CTA]) 2.54 ×10$^{-4}$ mol and [V-501]) 5.07×10$^{-5}$ mol. To ensure that the acid functional group on the monomer is neutralized, the pH of the polymerization solution may be adjusted to about 8.4 by the addition of NaOH. The monomer/chain-transfer agent, [M]/[CTA], ratios are chosen such that, at a quantitative conversion, number average degrees of polymerization (DPn) of 73 and 93 are attained, with [M] at 0.022 and 0.026 mol, respectively. Polymerizations may be conducted under nitrogen in a 22 mL reaction vial equipped with a magnetic stir bar. Polymers are purified by dialysis against deionized water and isolated by lyophilization.

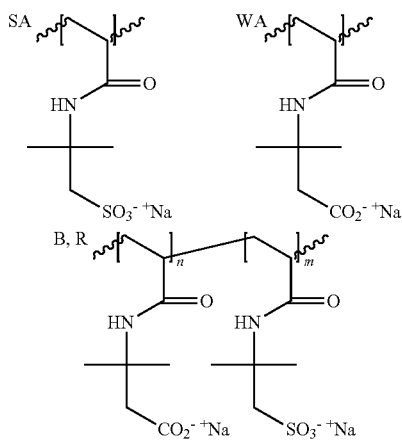

Reverse-Micelle Forming Anionic Surfactants

Compounds embodying the principles of the invention include anionic surfactants that form reverse micelles. Such anionic surfactants may be double-tailed or otherwise favor organic solvent solubilization over aqueous solubilization, and include sulfosuccinate diesters, sulfosuccinate monoesters, sulfosuccinimates, sulfo gluconate diesters, phosphoric acid monoesters, phosphoric acid diesters, and anionic Gemini surfactants. If an article in which the surfactant is to be incorporated is a poly(2-ethylhexylmethacrylate) polymer or copolymer, sodium bis(2-ethylhexyl)sulfosuccinate is a good choice of anionic surfactant because the surfactant is soluble in the liquid monomer solution and is reasonably soluble in the resulting polymer.

Sulfosuccinate diesters are most easily derived from maleic acid anhydride by reacting with an excess of the desired alcohol at 50-100° C. in the presence of a solvent (tolune, xylenes) to azeotropically remove the water produced and a catalyst, such as p-toluenesulfonic acid, followed by sulfonation in an aqueous solution of sodium hydrogen sulfite. Drying produces the solid. Sulfosuccinate monoesters are similarly obtained from the desired alcohol, but without solvent at 70-100° C. using a 1:1 stoichiometry.

Sulfosuccinamate diesters are derived from maleic acid anhydride by reacting with the desired amine in the presence of a catalyst, such as p-toluenesulfonic acid, followed by sulfonation in an aqueous solution of sodium hydrogen sulfite. Drying produces the solid. Sulfosuccinamate monoesters are similarly obtained from the desired amine, but using a 1:1 stoichiomery.

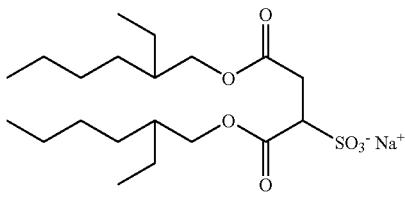

NaAOT, sodium bis(2-ethylhexyl)sulfosuccinate

The preparation of ammonium and tetrapropylammonium salts of bis(2-ethylhexyl)sulfosuccinate have been reported by Eastoe et al. (*Langmuir* 1993, 9, 2820-2824). A cation exchange resin (Amberlite IR 120 Plus, 2.0 mequiv g) is converted to its H$^+$ form by equilibration with 1.0 M HCl. A 50 mL sample of a 1.0 M ethanolic solution of Na(AOT) is passed through the column and the H$^+$ form of the surfactant produced. The first 20 mL of eluant is discarded; the remainder is reacted in situ to pH 7.0 with an aqueous solution of the quaternary ammonium hydroxide (Sigma-Aldrich, St. Louis, Mo., U.S.A.). During the reaction the pH is maintained in the range 5.0-8.5 and the solution continually stirred. The surfactant is obtained by evaporating the organic phase to dryness (Buchi rotary evaporator) at 35° C.; residual water is removed in a vacuum oven at 35° C. for 3 days. The dry products are obtained as white waxy solids.

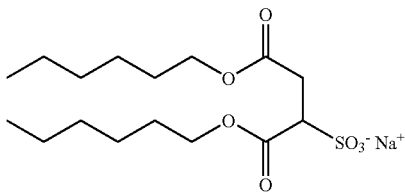

di-C$_6$SS, sodium bis(hexyl)sulfosuccinate

The straight chain and branched compounds may be prepared in a similar way from the appropriate starting alcohol, as described in Sandrine Nave and Julian Eastoe, and Jeff Penfold, *Langmuir* 2000, 16, 8733-8740). Butan-1-ol, pentan-1-ol, hexan-1-ol, heptanol-1-ol, octan-1-ol, 2-ethyl-1-hexanol, 2-propyl-1-pentanol, 2,4,4-trimethyl-1-pentanol, 3,5,5-trimethyl-1-hexanol, 4-methyl-3-heptanol, and 6-methyl-2-heptanol may be purchased from Sigma-Aldrich (St. Louis, Mo., U.S.A.). As an example the synthesis of di-C$_4$SS is outlined below. Briefly, fumaryl chloride (Avocado, 95%) is added dropwise to a stirred solution of butan-1-ol in dry tetrahydrofuran (THF; Aldrich, 99+% anhydrous). The reaction mixture is then refluxed until TLC indicated completion. After rotary evaporation of THF, the mixture is dissolved in diethyl ether and washed several times sequentially with 10% HCl and saturated NaHCO$_3$ solutions. The ethereal extracts are dried over anhydrous MgSO$_4$ and filtered, and diethyl ether is removed by rotary evaporation. Vacuum distillation yields the pure diester, which is a yellow oil. This is then dissolved in a 1:1 mixture of ethanol/water and refluxed with a slight excess of sodium metabisulfite and sodium sulfite (Avocado, 97%) to form the dibutyl sulfosuccinate. Soxhlet extraction with ethyl acetate, followed by several centrifugation cycles in methanol, may be employed to remove residual sodium salts. All the di-CnSS surfactants may be further recrystallized from methanol. The final products may be dried in a vacuum oven (50° C., 5 mbar) for at least 24 h, and then stored in a desiccating cabinet over phosphorus pentoxide, in sealed vials.

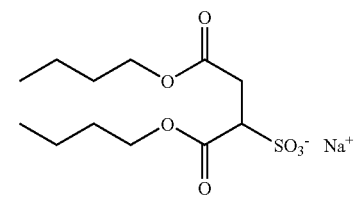

di-C4SS, sodium bis(butyl)sulfosuccinate

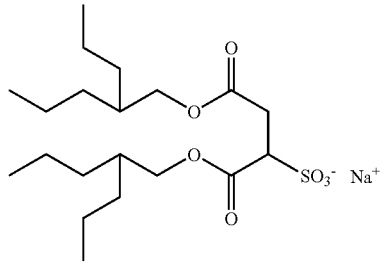

Sodium bis(2-propylpentyl)sulfosuccinate

Dickson et al. (*Ind. Eng. Chem. Res.* 2005, 44, 1370-1380) reported the synthesis of the phosphate diester, di(2,4,4-TMC5)phosphate$^-$ NH$_4^+$. A flask containing 2,4,4-trimethylpentanol (6.11 mL) and triethylamine (6.0 mL) dissolved in 30 mL of diethyl ether is degassed with argon and cooled to 0° C. This solution is slowly cannulated into an argon-degassed solution at 0° C. containing 1.79 g of phosphorus oxychloride in 30 mL of diethyl ether. A white precipitate forms upon addition. This solution is stirred overnight while slowly being warmed to room temperature. The triethylamine hydrochloride salt is filtered, washed with 50 mL of diethyl ether, and discarded. The diethyl ether and excess triethylamine are removed via rotary evaporation, leaving a yellow oil. This oil is dissolved in 40 mL of acetonitrile followed by slow addition of 3 mL of distilled water with stirring. After approximately 7 h, the excess water and acetonitrile are removed via rotary evaporation, providing 4.9 g of crude product. The oil is dissolved in chloroform and purified by being passed through a silica gel column, starting with chloroform as the mobile phase and changing to a 9:1 chloroform/methanol mixture. To produce 2,4,4-TMC5—PO$_4^-$NH$_4^+$, the resulting yellow oil is dissolved in 50 mL of ethanol, and a solution of ammonium hydroxide (0.65 mL of glacial NH$_4$OH in 10 mL of methanol) is added dropwise to the solution and stirred overnight. A whitish solid, trichained phosphates, is filtered and discarded, and the filtrate was concentrated via rotary evaporation. The resulting solid is dissolved in 100 mL methanol with 1 g of decolorizing carbon and stirred for 1 h. The carbon is filtered, and the solvent is removed via rotary evaporation. The crude product is dissolved in a minimum amount of methanol, and acetone precipitated the white gel-solid. To produce 2,4,4-TMC5—PO$_4^-$ N(CH$_3$)$_4^+$, the yellow oil is dissolved in 50 mL of ethanol, and 6.76 mL of tetramethylammonium hydroxide (25 wt % in methanol) is added dropwise and stirred overnight. No solids typically form. Consequently, the material is concentrated via rotary evaporation. The resulting gel-solid is dissolved in 100 mL of methanol with 1 g of decolorizing carbon and stirred for 1 h. The carbon is filtered, and the solvent is removed via rotary evaporation. The crude product is dissolved in a minimum amount of methanol, and acetone precipitated bright white crystals.

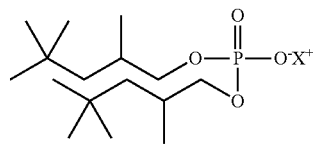

Di(2,4,4-TMC5)phosphate $^-$NH$_4^+$

The synthesis of 1,2-dilauroyl-sn-glycero-3-phosphatidyluridine was reported by Francesca Baldelli Bombelli, Debora Berti, Uwe Keiderling, and Piero Baglioni, (*J. Phys. Chem. B* 2002, 106, 11613-11621). 1,2-Dilauroyl-sn-glycero-3-phosphocholine may be purchased from Avanti Polar Lipids (Alabaster, Ala., U.S.A.), and its purity may be checked by TLC. DLPU may be synthesized starting from the corresponding phosphatidylcholine in a two-phase system according to the method proposed by Shuto and co-workers (*Chem. Pharm. Bull.* 1988, 35, 209-217) and obtained as an ammonium salt.

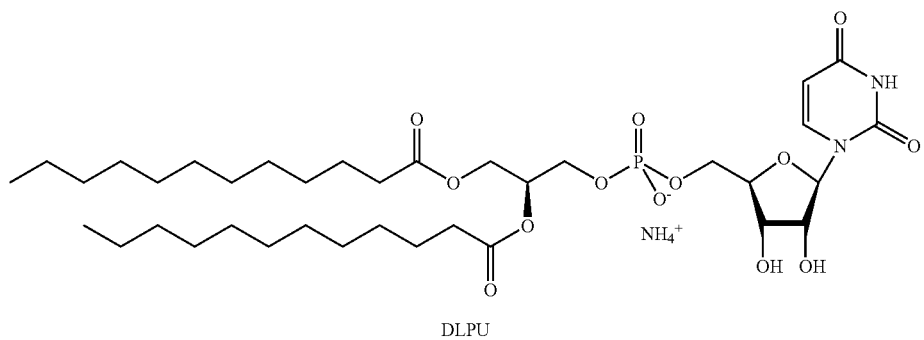

DLPU

The effect of carbon number has been studied (A. K. Chattopadhyay, D. O. Shah, and L. Ghaichao, *Langmuir* 1992, 8, 21-30) and example syntheses were demonstrated (A. K. Chattopadhyay, U.S. Pat. No. 4,919,179, incorporated herein by reference) with three different series of double tailed surfactants, viz. poly(isobutylene)succinic anhydride esterified with di- and triethanolamine esters of n-alkylsuccinic anhydride and poly(isobutylene)succinic anhydride esterified with ((n-alkyloxy)propyl)diethanolamine. The primary hydrocarbon chain of the surfactants comprises polyisobutylene of approximately 34 backbone carbon number and the secondary hydrocarbon chain comprises n-alkyl groups varying from C$_8$ to C$_{20}$. Poly(isobutylene)succinic anhydride of average molecular weight 1050 (supplied by Paramins Exxon, Linden, N.J., U.S.A.) may be further purified by chromatographic separation in order to avoid contaminations from free oils or poly(isobutylene) components. ((n-Alkyloxy)propyl) diethanolamines of Tomah Products (Milton, Wis., U.S.A), n-alkylsuccinic anhydride of Humphrey Chemicals (North Haven, Conn., U.S.A.), and reagent grade di- and triethanolamines (BDH) are used without any further purification. Surfactants of Series A may be synthesized by reacting diethanolamine with poly(isobutylene)succinic anhydride (PIBSA) followed by reaction with n-alkylsuccinic anahydride. With $R_2$=tetradecyl, 29.6 g of tetradecylsuccinic anhydride is heated to a 60-65° C. Then 10.5 g of diethanol amine is added dropwise to the anhydride with constant stirring. Completion of reaction and formation of esters is noted by IR spectroscopy by the disappearance of the absorbance peak at 1790 $v^{-1}$ due to anhydrides and appearance of the ester peak at 1740 $v^{-1}$. Further reaction between PIBSA and the adduct is carried out by using all of the above reaction products together with 167 g of PIBSA. The surfactant is produced as a 50% w/w solution in paraffin oil; and conversion to alkali salts is done by titration with MOH, where $M^+$ is an alkali cation. Surfactants of Series B are synthesized by reacting triethanolamine with n-alkylsuccinic anahydride followed by reaction with poly(isobutylene)succinic anhydride. For example, 26.8 g of dodecylsuccinic anhydride is heated to a temperature in the range of 60-65° C. Then 14.9 g of triethanolamine is added dropwise to the anhydride with constant stirring. Completion of reaction and formation of esters is noted by the same way as described for Series A. Further reaction between PIBSA and the adduct may be carried out by using all of the above reaction products together with 167 g of PIBSA. The surfactant is produced as a 50% w/w solution in paraffin oil; conversion to alkali salts is done by titration with MOH, where $M^+$ is an alkali cation. Surfactants of Series C are synthesized by reacting ((n-alkyloxy)propyl)diethanolamine with poly(isobutylene)succinic anhydride at 80° C. Conversion to alkali salts is done by titration with MOH, where $M^+$ is an alkali cation.

Series-A

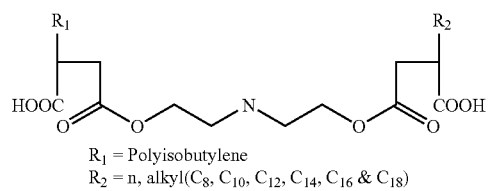

$R_1$ = Polyisobutylene
$R_2$ = n, alkyl($C_8$, $C_{10}$, $C_{12}$, $C_{14}$, $C_{16}$ & $C_{18}$)

Series-B

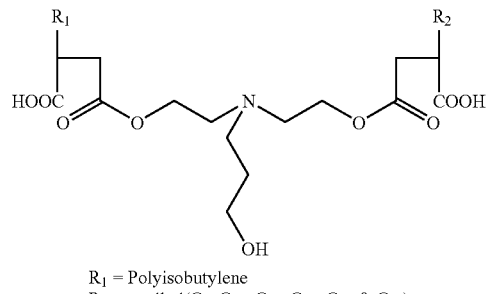

$R_1$ = Polyisobutylene
$R_2$ = n, alkyl($C_8$, $C_{10}$, $C_{12}$, $C_{14}$, $C_{16}$ & $C_{18}$)

Series-C

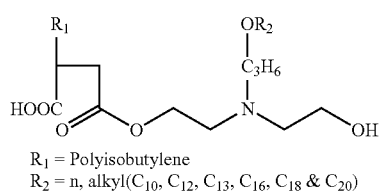

$R_1$ = Polyisobutylene
$R_2$ = n, alkyl($C_{10}$, $C_{12}$, $C_{13}$, $C_{16}$, $C_{18}$ & $C_{20}$)

Gemini surfactants consist of two surfactant moieties, linked together by a spacer unit such as 2, 3, 4, or more methylene groups. Gemini anionic surfactants based on EDTA (Laurent Wattebled and André Laschewsky, Colloid Polym Sci (2007) 285: 1387-1393) such as the didecyldimethyl amido derivative pictured below are obtained by reaction of secondary amines with EDTA anhydride. N-methyldodecylamine (3.20 g, 16 mmol) and EDTA anhydride (2.05 g, 8 mmol) suspended in $CH_3OH$ (50 ml) are reacted for 22 h at 40-45° C. The anhydride particles progressively disappear as the reaction progresses. After cooling of the sample to room temperature the remaining particles are filtered off. The reaction mixture is evaporated to give a yellowish oil. Acetone is then added until a white solid precipitates. The precipitate is filtered off and is further purified by dissolution in $CHCl_3$ and precipitation in acetone to yield a white powder. Finally, the intermediate product is neutralized with sodium hydroxide (1 M aq, 2 equivalents), and the obtained solution is freeze-dried to give gemini surfactant in quantitative yield a colorless, hygroscopic powder.

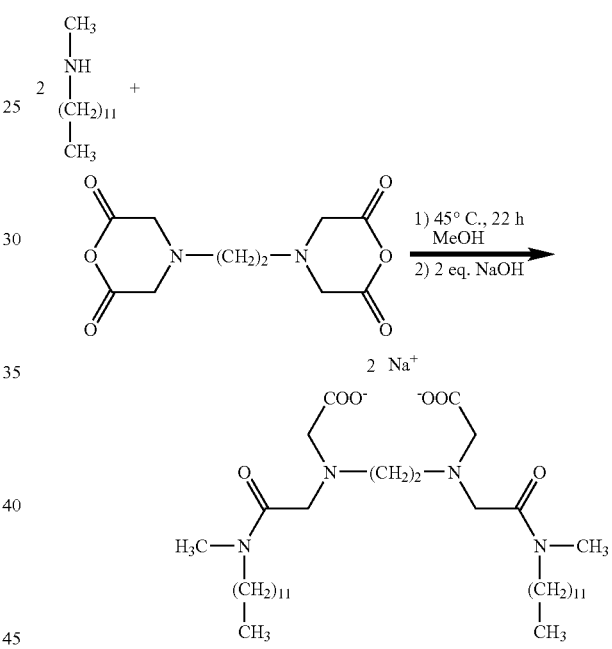

Other substituents may be incorporated by simply varying the starting amine $RNH_2$ or $R_1R_2NH$, where R, $R_1$, and $R_2$ are alkyl, alryl, alkylaryl, or otherwise chosen to make the surfactant compatible with particular choices of solvent, polymer, and final composition. Straight chain and branched carbon chains of 6-18 carbon atoms are preferred for the primary amines, and a total of 4 to 10 carbon atoms for each of $R_1$ and $R_2$ combined are preferred for the secondary amines when high solubility in nonaqueous environments is desired. The cation may be varied by choosing an appropriate hydroxide solution, such as LiOH, KOH, or tetramethylammonium hydroxide, etc.

Other anionic Gemini surfactants are described by S. K. Hait and S. P. Moulik (Current Science, Vol. 82, No. 9, 10 May 2002, pp. 1101-1111):

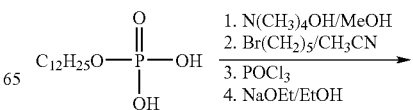

-continued

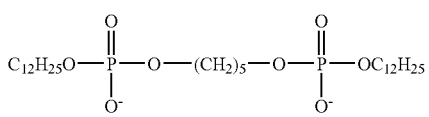

The following Gemini phosphate esters were reported by Menger and Littau (J. Am. Chem. Soc, 1991, 113, 1451-1452). They may be synthesized by first reacting α,α'-dibromo-p-xylene with dianionic alkyl phosphate monoesters.

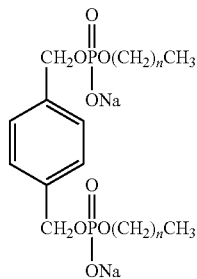

Menger and Littau also reported the photosensitive styryl Gemini phosphate ester prepared by phosphorylating the spacer diol with $POCl_3$, and then reacting the intermediate with long chain alcohols.

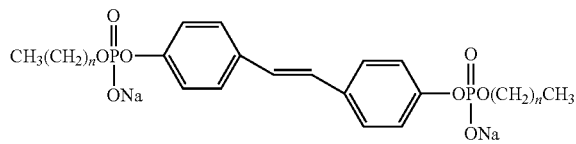

The following Gemini sulfate and sulfonates have ethylenoxide spacers.

TABLE 1

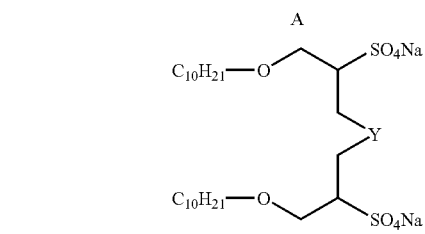

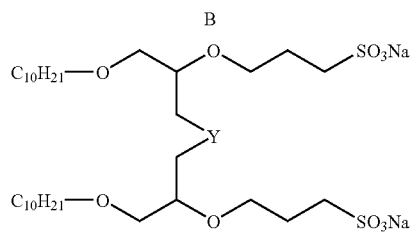

Properties of Gemini sulfates (A) and sulfonates (B) in comparison with sodium laurylsulfate and sodium laurylsulfonate.

| Compound[a] | Y | CMC/mM | $\gamma_{cmc}$/N m$^{-1}$ | $C_{20}$/mM |
|---|---|---|---|---|
| A | —OCH$_2$CH$_2$O— | 0.013 | 27.0 | 0.001 |
| C$_{12}$H$_{25}$SO$_4$Na | — | 8.2 | 39.5 | 3.1 |
| B | —O— | 0.033 | 28.0 | 0.008 |
| B | —OCH$_2$CH$_2$O— | 0.032 | 30.0 | 0.0065 |

TABLE 1-continued

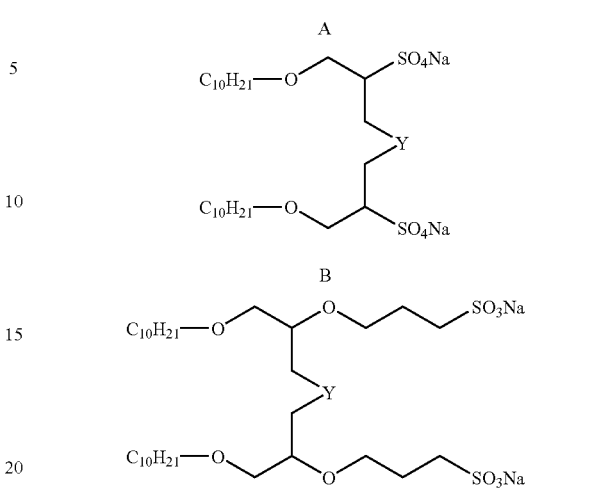

Properties of Gemini sulfates (A) and sulfonates (B) in comparison with sodium laurylsulfate and sodium laurylsulfonate.

| Compound[a] | Y | CMC/mM | $\gamma_{cmc}$/N m$^{-1}$ | $C_{20}$/mM |
|---|---|---|---|---|
| B | —O(CH$_2$CH$_2$O)$_2$— | 0.060 | 36.0 | 0.01 |
| C$_{12}$H$_{25}$SO$_3$Na | — | 9.8 | 39.0 | 4.4 |

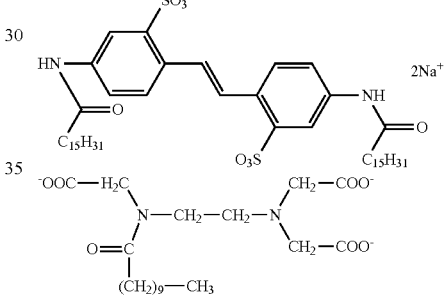

The double chain dicarboxylate forms vesicles (Jaeger, D. J. and Brown, E. L. G., *Langmuir*, 1996, 12, 1976-1980.). The reaction of threo diol ester 4 with α-keto ester 5 gives diastereomeric diester ketals 2. This mixture is converted into diacid ketals 3. A 1:1 mixture of surfactants 1a and 1b is generated in situ by the dispersal of 3 into a pH 9.2 or 10.7 KHCO$_3$—K$_2$CO$_3$ buffer. The potassium surfactants are more soluble than the sodium surfactants.

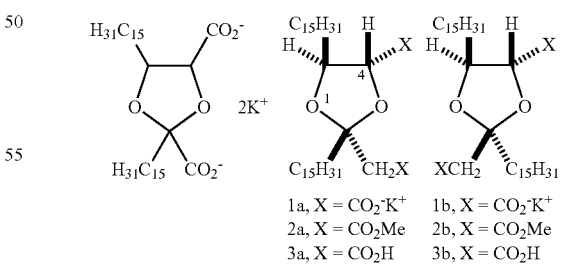

1a, X = CO$_2$$^-$K$^+$  1b, X = CO$_2$$^-$K$^+$
2a, X = CO$_2$Me  2b, X = CO$_2$Me
3a, X = CO$_2$H  3b, X = CO$_2$H

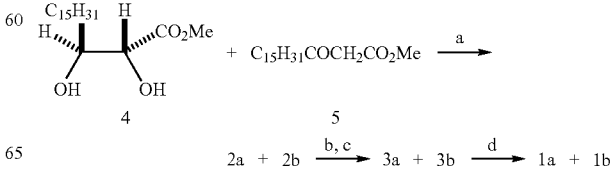

The triple-chained di-carboxylate below (Sumida, Y. et al., *Chem. Commun.*, 1998, 2385-2386) can sequester metal ions effectively.
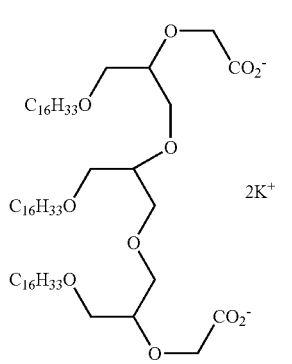
B
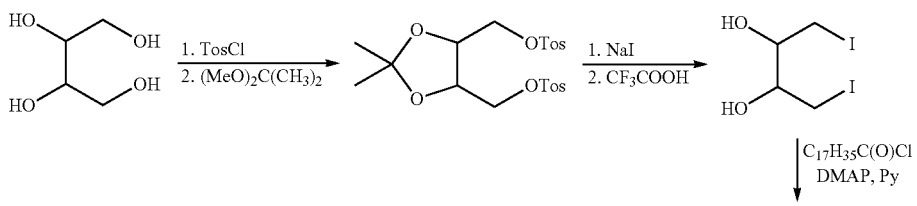
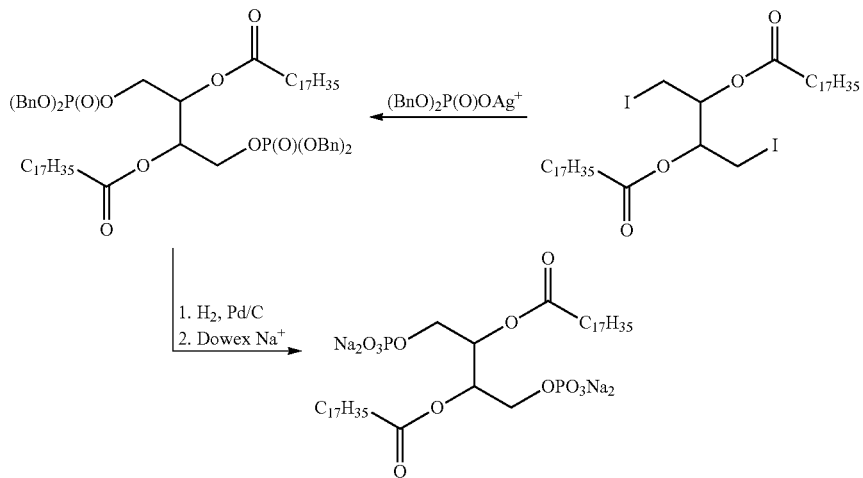
Tos = toluene-4-sulfonyl
Syntheses of fluorinated phosphate diesters (S. Jason et al., *Langmuir* 2004, 20, 1065-1072) F/F and H/F,
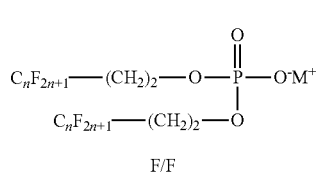
F/F
-continued
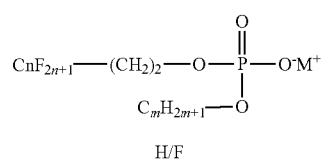
H/F are outlined below:

F/F Surfactants

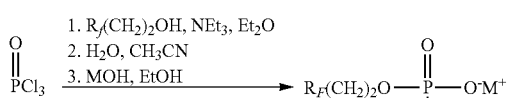

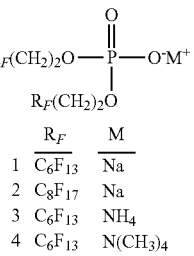

| | $R_F$ | M |
|---|---|---|
| 1 | $C_6F_{13}$ | Na |
| 2 | $C_8F_{17}$ | Na |
| 3 | $C_6F_{13}$ | $NH_4$ |
| 4 | $C_6F_{13}$ | $N(CH_3)_4$ |

H/F Surfactants

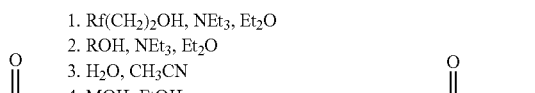

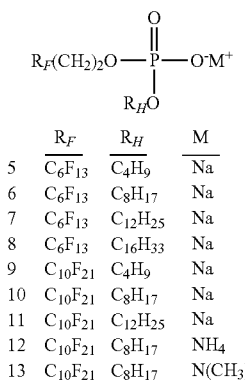

| | $R_F$ | $R_H$ | M |
|---|---|---|---|
| 5 | $C_6F_{13}$ | $C_4H_9$ | Na |
| 6 | $C_6F_{13}$ | $C_8H_{17}$ | Na |
| 7 | $C_6F_{13}$ | $C_{12}H_{25}$ | Na |
| 8 | $C_6F_{13}$ | $C_{16}H_{33}$ | Na |
| 9 | $C_{10}F_{21}$ | $C_4H_9$ | Na |
| 10 | $C_{10}F_{21}$ | $C_8H_{17}$ | Na |
| 11 | $C_{10}F_{21}$ | $C_{12}H_{25}$ | Na |
| 12 | $C_{10}F_{21}$ | $C_8H_{17}$ | $NH_4$ |
| 13 | $C_{10}F_{21}$ | $C_8H_{17}$ | $N(CH_3)_4$ |

To synthesize $diH_8$—$PO_4^-$ $Na^+$ [di($CF_3(CF_2)_4CH_2CH_2$) phosphate$^-$ $X^+$] (Jasper L. Dickson et al., *Ind. Eng. Chem. Res.* 2005, 44, 1370-1380), phosphorus oxychloride (1.79 mL) may be first added via syringe to 30 mL of anhydrous diethyl ether, under argon. The mixture is cooled to 0° C., and a cold solution of 1-octanol (6.05 mL) and triethylamine (5.82 g) in 25 mL of diethyl ether is slowly added via cannula, giving white precipitate, triethylamine hydrochloride salts. The solution is allowed to warm to room temperature and stirred under argon overnight. The triethylamine hydrochloride salts are filtered and washed with 50 mL of diethyl ether. The solvent and excess triethylamine are removed via rotary evaporation, and the product is dissolved in 40 mL of acetonitrile and 1 mL of water and stirred overnight. The product is collected via rotary evaporation and identified as the neutral phosphate using NMR spectroscopy. After the product is dissolved in 40 mL of ethanol, a mixture of aqueous NaOH (0.17 ML, 50 wt %) dissolved in 25 mL of ethanol is added dropwise to the stirring phosphate solution. After being stirred overnight, the product is filtered, and acetone is added to induce precipitation of a white salt, which is filtered and rinsed with 30 mL of acetone.

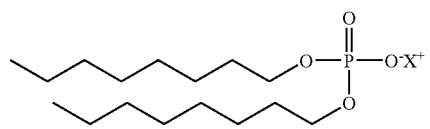

Di($CF_3(CF_2)_4CH_2CH_2$)phosphate $^-X^+$

Anionic surfactants according to the invention further include the following, wherein $M^+$ is a metal cation:

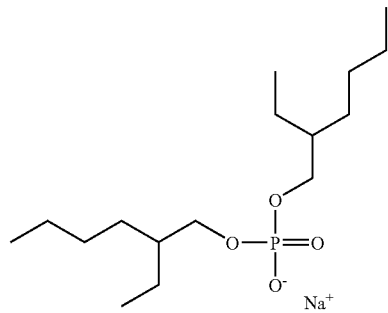

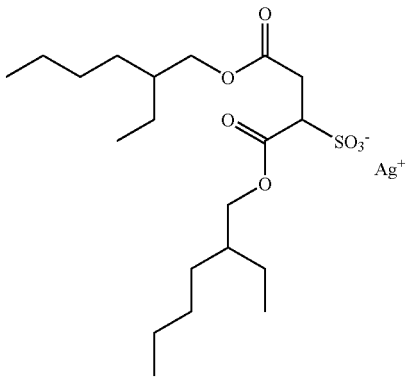

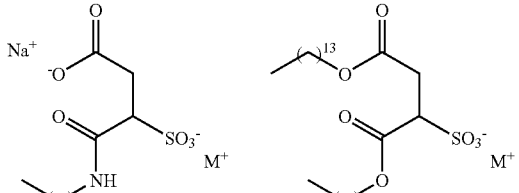

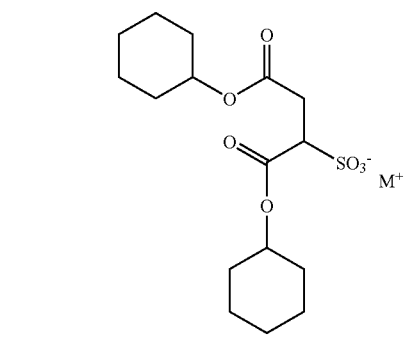

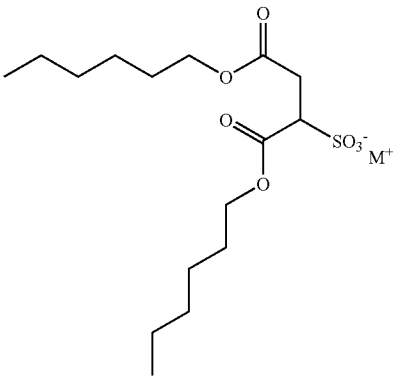

Silver Anionic Surfactants and Silver Anionic Polyelectrolytes

Anionic surfactant salts according to the invention may be changed from one cationic form to another cationic form, for example, from the sodium to the silver form. Suitably, sodium surfactants may be converted to acid form using ion exchange or ion exchange chromatography, as described in Petit et al. (1993) *J. Phys. Chem.* 97: 12974-12983, hereby incorporated by reference. Resins for the ion exchange may suitably include protonated strong cationic exchange resins such as Lewatit SP 1080 (LANXESS, Pittsburgh, Pa., U.S.A.). The acid form may then be loaded onto a weakly acidic macroporous cation exchange resin, such as Bio-Rex 70 (BIO-RAD, Hercules, Calif., USA) loaded with silver ion. An eluent of a 50/50 mixture of water and ethanol may be used. The final product may be dried under vacuum. The efficiency of the conversion of ions may be determined by silver ion concentration titration using VoPhard's method, with the precipitation of thiocyanate in the presence of ammonium ferric sulfate as the indicator. Alternatively, a simple potentiometric tirtration with standard chloride in methanol or methanol/water may be done using a silver, silver halide, or silver sulfide indicating electrode, and any suitable and convenient reference electrode, such as AgCl, with any suitable salt bridge.

An alternative approach to producing anionic surfactants in the silver form may be useful when the protonated or acid form of the surfactant is readily available. The acid form, in any suitable solvent, is stirred with an equivalent of silver oxide (silver hydroxide, silver oxyhydroxide). The by product is water.

Additionally, simple conversion from alkali metal form to the silver ion form may be accomplished by two phase ion exchange. The surfactant is dissolved in a convenient water immiscible solvent, such as diethylether, and combined with an equal volume of 0.1 M aqueous $AgNO_3$ in a separatory funnel. The alkali cation is extracted into the aqueous phase and the silver ion is extracted into the ether phase, sequestered by the surfactant. This washing is repeated several times, and then the ether phase is washed with water, and the phases are separated. The either phase is then reduced in volume on a rotary evaporator, and the remaining paste is dried in a vacuum oven at 25-50° C.

A similar method for effecting ion-exchange of cations in the anionic surfactants and polyelectrolytes of the present invention is the following method reported by Steytler et al. (*Langmuir* 1996, 12, 1483-1489). Bis(2-ethylhexyl)phosphoric acid (HDEHP, 97%, Aldrich) is initially purified according to the method of Partridge et al. (*J. Inorg. Nucl. Chem.* 1969, 31, 2587). The general method used to prepare all the multivalent di(2-ethylhexyl)phosphate (DEHP) metal salts involved neutralization of HDEHP with the metal hydroxide. In the case of divalent metals, $M(OH)_2$ is freshly prepared as a precipitate by mixing an aqueous solution of the metal nitrate (15 mL; 1 mol $dm^{-3}$) with excess aqueous sodium hydroxide solution (20 mL, 1 mol $dm^{-3}$). The $M(OH)_2$ precipitate is then filtered and thoroughly washed with water to remove excess NaOH. The metal hydroxide is then added directly to a biphasic system comprising water (50 mL) and a solution of HDEHP in diethyl ether (25 mL, 1.1 mol $dm^{-3}$) contained in a separating funnel. The resulting mixture is thoroughly shaken and left to phase separate overnight. The lower aqueous phase is then removed, together with any excess M(OH)n present at the interface, and the ether layer is repeatedly washed with fresh aliquots of water and reduced in volume to about 15 mL. The $M^{n+}(DEHP^-)n$ salt is subsequently precipitated by the slow addition of acetone to the ether solution with stirring. After complete precipitation, the product is filtered and washed repeatedly with acetone. The $M^{n+}(DEHP^-)n$ salts are initially dried in a vacuum oven at 40° C. for about 48 h and further dried by storing over $P_2O_5$ in a vacuum desiccator until required.

Similar procedures applied to bis(2-ethylhexyl)sulfosuccinate are described by Eastoe et al. (*J. Phys. Chem.* 1993, 97, 1459-1463). The $M^+(AOT^-)$ surfactants (M=$K^+$, $Rb^+$, and $Cs^+$) may be prepared using the method due to Hatton (E. B Leodidis,; T. A. Hatton, In *Structure and Reactivity in Reversed Micelles*; M. P Pileni, Ed.; Elsevier: New York, 1989; p 270.). Briefly, approximately equal volumes of a 1.0 mol $dm^{-3}$ aqueous solution of the metal nitrate (Sigman-Aldrich, St. Louis, Mo., U.S.A.) with a 0.10 mol $dm^{-3}$ heptane solution of Na(AOT) are shaken together. On settling, a Winsor II microemulsion system may be formed: the organic upper phase is removed and shaken with fresh 1.0 mol $dm^{-3}$ metal nitrate twice more. The $M^+(AOT^-)$ surfactant is then obtained by evaporating the organic phase to dryness (Buchi rotary evaporator). The dry product is stored under vacuum over $P_2O_5$ (Aldrich) until used. The surfactants are analyzed for the extent of replacement of $Na^+$ for $Mn^+$ using either UV/vis or atomic absorption (Varian Spectra AA-10) spectrophotometry. The amount of residual water (x) in the product $M^+(AOT^-).xH_2O$ is assessed with a calibrated FTIR measurement of the integrated area of the absorbance due to the O—H stretch (3700-3050 $cm^{-1}$).

When the anionic polyelectrolyte is synthesized for a particular application, it may be expedient to use the acid monomers rather than alkali or ammonium cation salts of the monomer. After synthesis is complete the acid polymer is mixed with an equivalent amount of silver oxide in a suitable solvent, where the conversion is quantitative. The solvent and water produced are then removed by vacuum drying.

Alternatively, starting with alkali metal salts of anionic copolymer of styrene sulfonate, sodium salt, and styrene (25 mol % styrene sulfonate), the copolymer is dissolved in toluene and ion exchanged into the silver ion form by using the two-phase ion exchange process described above. An equal volume of 0.1 M silver nitrate is added to the toluene solution in a separatory flask, shaken, and exchanged twice more with aqueous silver nitrate, then washed twice with deionized water. The water phase is separated, and the toluene solution is reduced in volume, and finally dried in a vacuum oven at 50° C. overnight.

Formation of the Composition

A particular advantage of the method of inclusion of the silver ion monodentate ligand complexes of the present invention, in comparison to formulations of prior art silver nanoparticles and silver salt nanoparticles, is that the instant silver ion complexes dissolve in the solutions of the present invention as a result of chemical free energy reductions. Inclusion of nanoparticulate dispersions of silver are at best metastable, and extraordinary stabilization methods, nanoparticle formation methods, and high energy dispersing methods must be used to create useful formulations of such prior art silver sources. In the present invention, the silver surfactants and silver polyelectrolytes simply dissolve, as equilibration into the dissolved state is a negative free energy (i.e., spontaneous) process.

The particular solvent or solvent mixture to use is selected in order to optimize the method of application and the physical and chemical nature of the substrate to be contacted by the silver monodentate ligand containing solution. A prime consideration for applying silver surfactant and silver polyelectrolyte solutions of the invention is that said solution will wet the substrate. In cases where the desired wetting is at first not obtained, an alternative surfactant resulting in lower surface tensions of the solution may be used. Alternatively, fluorocarbon surfactants of the present invention may be added to the solution, in silver ion complexed form or with any other suitable cation. Inclusion of such fluorocarbon containing surfactants in said solutions will be of particular help in obtaining satisfactory wetting on plastic and other polymeric surfaces and substrates, including specialized coatings and enamels that are normally difficult to wet.

Some useful solvents of the invention are listed in Table 2 along with their corresponding surface tensions at or near room temperature. The selection of a solvent or solvent mixture may take account of ventilation requirements and possible safety hazards because of the flammability of some of the solvents. For example, water (sterile water) is a preferred solvent for delivering the surfactants of the invention to mammalian tissues. Isopropanol and ethanol may be mixed with water for delivery to and coating on exterior essentially intact skin tissue. For applications to open wounds, burns, and surgical cavities, sterile water and sterile aqueous saline are preferred in order to minimize untoward tissue dehydration.

TABLE 2

Useful Solvents and Their Surface Tensions.

| Solvent | Surface Tension (dyn/cm) |
|---|---|
| Trifluoroacetic Acid | 13.63 (24° C.) |
| Pentane | 15.48 (25° C.) |
| Ethyl Ether | 17.06 |
| Hexane | 17.91 (25° C.) |
| Iso-Octane | 18.77 |
| Acetonitrile | 19.10 |
| Methyl t-Butyl Ether | 19.4 (24° C.) |
| Heptane | 20.30 |
| Triethylamine | 20.66 |
| Isopropyl Alcohol | 21.79 (15° C.) |
| Ethyl Alcohol | 22.32 |
| Cyclopentane | 22.42 |
| Methanol | 22.55 |
| Isobutyl Alcohol | 22.98 |
| Acetone | 23.32 |
| Methyl Isobutyl Ketone | 23.64 |
| n-Propyl Alcohol | 23.70 |
| n-Butyl Chloride | 23.75 |
| Ethyl Acetate | 23.75 |
| Methyl Ethyl Ketone | 24.0 (25° C.) |
| n-Butyl Alcohol | 24.57 |
| Cyclohexane | 24.98 |
| n-Butyl Acetate | 25.09 |
| Methyl n-Propyl Ketone | 25.09 |
| Tetrahydrofuran | 26.4 (25° C.) |
| o-Dichlorobenzene | 26.84 |
| Chloroform | 27.16 |
| Dichloromethane | 28.12 |
| Toluene | 28.53 |
| o-Xylene | 30.03 |
| 2-Methoxyethanol | 31.8 (15° C.) |
| Ethylene Dichloride | 32.23 |
| Dimethyl Acetamide | 32.43 (30° C.) |
| o-Dichlorobenzene | 26.84 |
| Chloroform | 27.16 |
| Dichloromethane | 28.12 |
| Toluene | 28.53 |
| o-Xylene | 30.03 |
| 2-Methoxyethanol | 31.8 (15° C.) |
| Ethylene Dichloride | 32.23 |
| Dimethyl Acetamide | 32.43 (30° C.) |
| Chlorobenzene | 33.28 |
| 1,4-Dioxane | 34.45 (15° C.) |
| N,N-Dimethylformamide | 36.76 |
| Pyridine | 36.88 |
| Propylene Carbonate | 41.93 |
| Dimethylsulfoxide | 43 |
| Water | 72.8 |

In some cases, commercial surfactant formulations may be required in order to effect wetting of the solutions of the present invention on relatively low surface energy substrates and surfaces. Table 3 lists a series of hydrocarbon/fluorocarbon solvents, Vertel® solvents, available from the DuPont Corporation through Micro Care Company (Bristol, Conn., U.S.A.).

TABLE 3

Commercially Available FluoroHydrocarbon Solvents and Their Surface Tensions.

| Solvent | Surface Tension (dyn/cm) |
|---|---|
| Vertel ® XF | 14.1 |
| Vertel ® XM | 14.1 |
| Vertel ® XDA | 14.1 |
| Vertel ® XP10 | 14.1 |
| Vertel ® XMS Plus | 14.9 |
| MicroCare CF | 15.0 |
| Vertel ® XP | 15.1 |
| Vertel ® MCA | 15.2 |
| Vertel ® SMT | 15.5 |
| Vertel ® MCA Plus | 16.1 |
| Vertel ® CCA | 18.8 |
| Vertel ® CMS | 19.2 |
| Vertel ® CHD | 19.4 |

Methods of Applying the Composition

The solutions of the present invention are intended to be delivered onto and into surfaces and substrates of materials so as to eradicate any bacteria already present on and in such surfaces and substrates by the bactericidal activity of the invention surfactants and complexes. It is also anticipated that once applied to a surface or substrate that prophylactic protection against bacteria coming to reside on or in said surfaces and substrates will continue for such time until coating is removed.

Spraying the solutions of the invention onto and into surfaces and substrates may be done by any normal means of spraying. For example, in the case of spraying into shoes, onto shirt underarm areas, and into sports uniforms between launderings, small (5-100 mL) hand held sprayers may be used, whereby the aerosol is generated by finger pressure on a nozzle/pump assembly. As the area and magnitude of area and materials increases, larger spray bottle may be used, for example wherein the pump driving the aerosol generation is pumped by a handle activated by four of the fingers in a hand. If walls, ceilings, and their attached fixtures are to be sprayed, larger volume pressurized sprayers are preferred. Spraying is a suitable method for applying the solutions of the present invention to fabrics, particularly to moving webs of fabric. Arrays of spray nozzles can be used to coat the solutions onto and into the fabric in a uniform manner.

Pouring is a suitable way to apply the solutions and fluids of the present invention to a small to large horizontal area. In the case of small areas, the pouring method may be augmented with wiping, coating, or spinning. In the case of larger areas, the pouring method may be augmented by squeegee blades of the type, for example, used in washing windows. The contact edges of said squeegee blades may be modified with grooves and slits so as to insure a given thickness of fluid remains on the surface after passing the blade over the surface.

Where the volume or weight of solution or composition administered is controlled, metering may be used to apply the compositions of the present invention for inhalation treatments, where the amount of aerosol dosing the lungs may be important to control. Metering may also be used to control flow and coating amounts in combination with pumping, filling, and coating methods of application.

Coating is a suitable application method for sheet materials and fabrics suitable for continuous web treatment. Doctor blade, x-hopper, slide hopper, gravure, and curtain coating are preferred methods of coating the solutions and fluid compositions of the present invention to sheet materials and fabrics. Dip coating is a suitable method for coating small to intermediate sized object and materials. Dip coating is a suitable method for coating fabrics that are absorbent.

Pumping may be used to move the solutions and fluid compositions of the present invention from a reservoir or holding tank to a spray nozzle, x-hopper coating surface, slide hopper coating surface, or curtain coating apparatus. Hand operated spraying may incorporate a finger or hand actuated pump.

Wiping using absorbent cloths, sponges, and other absorbent materials that infuse the solutions of the invention and then exude them onto a contacting surface when pressed against said surface may be used to apply the compositions of the invention to walls, counter tops, shelving, windows, window sills, tables, and other objects. On larger surfaces a volume may be applied with a sponge and then the applied volume is spread over a larger area by action of a hand operated blade.

Flowing is a suitable method of application when the invention solutions are to be applied to a continuously moving web, such as in an operation of x-hopper or slide hopper coating are as in curtain coating. Another approach may be where a large volume spray is directed along the top of a wall area, and the rest of the wall is covered by allowing the impacting solution to simply flow down the wall, wetting the lower portions as the vertically flow proceeds.

Drying

After application of the solutions and fluids of the present invention, the surfaces and substrates to which these solutions and fluids have been applied may be dried. Evaporation is a suitable method of drying. In manufacturing environments where air quality and safety are paramount, temperature programmed drying, heating, and solvent recovery may be important components to the overall process. Heating may be necessary when solvents with relatively high boiling points are used.

Surfaces and Substrates

The surfaces and substrates to which the solutions and compositions of the present invention range from those encountered in the practice of medicine with human tissue and in veterinary medicine with animal tissues of every type, including severely burned epidermis and dermis tissues, open wounds in the category of scrapes and scratches, incisions encountered in surgery, lung, nasal, and vaginal mucosal tissues, abdominal and thoracic tissues line the organs and cavities of the abdomen and chest cavity, bone fracture surfaces, and surfaces lining the mouth, gums, ears, urethra, and skin surfaces, to the surfaces and substrates encountered in the interiors of homes, schools, hospitals, manufacturing plants, and other public places of business and government.

Existing wound dressing materials of woven and sheet form include surfaces and substrates to which the solutions and compositions of the present invention can be applied. The threads and strands used in making such woven materials may be coated with the solutions and compositions of the present invention by dip coating during the spinning and weaving processes during manufacture. Alternatively, the compounds of the present invention may be incorporated into the bulk of the synthetic material prior to spinning such polymers into strands and threads to be woven into would dressings.

All clothing articles that come in contact with sweat and bacteria normally populating human skin are objects benefiting from the present invention. Fabrics and shoes may be treated with the solutions and compositions of the present invention by spraying, dip coating, and wiping. Alternatively, the materials comprising the contact surfaces of clothing articles may incorporate the surfactants and polymers of the present invention during their manufacture, so that they exude bactericidal activity over a continuing time interval. Applications to textiles in general may be made either to the final product by one or more application methods of the present invention or they may be incorporated directly into polymeric compositions used to prepare synthetic fabrics.

Surface and substrates in the home are also anticipated as targets for the solutions and fluid compositions of the present invention. Wall and ceiling, as well as all objects and fixtures attached thereto, are possible places for bacteria and microbes to inhabit. Kitchen and bathroom walls, ceilings, and fixtures attached thereto, as well as shelving, cabinetry, are examples of surfaces to which to apply the solutions and fluid compositions of the present invention. Similarly in the kitchen and laundry, ceilings and walls and the fixtures attached thereto, counter tops, open and closed shelving, cabinetry, stoves, refrigerators, washing machines, drying machines, microwave ovens, and furniture are examples of objects with surfaces to which to apply solutions and fluid compositions of the present invention.

Similarly in places of business, government, and public education there are walls and ceilings, fixtures attached thereto, banisters, doors, windows, furniture, lockers, rest rooms, auditoriums, vestibules, cafeteria and snack shop areas, and other surfaces and substrates to which the solutions and fluid compositions of the present invention may be applied.

Hospitals, medical centers, doctor's offices, and health centers are an additional class of places that comprise walls, ceilings, fixtures attached thereto, operating rooms, waiting rooms, rest rooms, bath rooms, laboratories, hallways, nurse's stations, patient rooms, windows, window treatments, diverse curtains, doors, cabinetry and diverse appliances, machinery, and equipment that exhibit surfaces and substrates to which the solutions and fluid compositions of the present invention may be applied.

Certain substrates of the present invention are themselves liquid suspensions and solutions. Topical creams for treating wounds, yeast infections, acne, superficial burns are suitable substrates to which the solutions, fluids, and compounds of the present invention may be usefully applied.

Polymer Binders and Resins

The compounds of the present invention may be suitably incorporated into a microemulsion of immiscible monomers and form polymeric coatings by microemulsion polymerization, as described in Texter et al. (2004) *Macromolecules* 37: 5841-5843; (2005) Correction 37: 7424, hereby incorporated by reference. Microemulsion polymerization is a method for formulating polymer coatings from immiscible monomers. Microemulsions are thermodynamically stable solutions of at least two immiscible fluids, such as oil and water, made miscible by the action of a third chemical component, suitably a surfactant such as silver bis[2-ethylhexyl]sulfosuccinate or sodium bis[2-ethylhexyl]sulfosuccinate. For example, a polyurethane coating may be made from a microemulsion of propylene glycol and isophorone diisocyanate fluids. The microemulsion may contain equivalent weights of two different monomers, for example, propylene glycol and isophorone diisocyante, to make polyurethane. Polyurethanes may form by addition step polymerization of diols with diisocyanates. Cross-linking agents may be included in the reaction to increase the molecular weight of the polymer. A reverse microemulsion or reverse micelle may also be formed. Suitably, compounds of the invention form reverse micelles.

The polymer binders and resins of the inventions may be any of the type included in commercially available paints and other protective coating formulations, wherein the binder comprises organic or partially organic polymeric components or wherein the binder comprises precursors to polymers, wherein such precursors transform to the final binder upon drying or curing of the paint or coating formulation.

The polymeric coatings may be hydrophobic. The polymeric binder in the form of precursors may be included in the coating composition of bactericidal composition in the form of monomers in a microemulsion of in the form of a solution. The microemulsion may further include at least about 5% to at least about 50% of silver anionic surfactant by weight relative to the weight of all monomers and anionic surfactant. The microemulsion may include less than about 95% to less than about 50% silver or sodium anionic surfactant. Suitably, the microemulsion includes about 0.01 to 3% silver anionic surfactant by weight relative to the weight of all monomers and anionic surfactant. The microemulsion may also include more than one cationic form of the anionic surfactant. For example, a 30% anionic surfactant microemulsion may contain 10% silver anionic surfactant and 20% sodium anionic surfactant, or 1% silver anionic surfactant and 29% sodium anionic surfactant, or 0.1% silver anionic surfactant and 29.9% sodium anionic surfactant. The microemulsion is suitably placed on a surface and thereon cured by heating or by UV irradiation to form a polymeric coating on the surface. Suitable surface materials include ceramics, glass, metal such as aluminum and steel, plastics, and wood. Suitable surfaces and substrates include any material in the consumer, industrial, and government arena that benefits from a decorative or protective coating. A catalyst may be added to the microemulsion to drive polymerization on a surface. Suitable catalysts include dibutyltin dilaurate (DBTD).

The polymeric coatings in accordance with the invention may be at least about 1 µm thick to at least about 500 µm thick as needed for the protective application. Suitably, the polymeric coating may be about 5 to 50 µm thick. The polymeric composition in accordance with the invention may contain about 0.0001% to about 1.0% metal cation, suitably about 0.0001% to about 1.0% $Ag^+$, by weight of the total composition.

Polymeric Compositions

Polymer compositions of the invention include a plurality of thermoplastic polymers that may be used to form objects useful in the consumer, industrial, and healthcare industries. Such objects may be made by any appropriate means of fabrication, including extrusion, injection molding, blow molding, casting, and solvent casting. Such objects may include bottles for storing foods, liquids, cosmetics, and perishable items. They may also include polymers to be fabricated to catheters and tubing, artificial joints, bags, and packaging materials. In these types of compositions, the silver compounds of the invention may be incorporated at appropriate levels, determined by experimentation illustrated in the examples, during the polymer formation process. Alternatively, the silver compounds of the invention may be incorporated by swelling the polymer in a suitable solvent containing the silver compounds, and allowing the object to dry. This process may provide a gradient of active silver in the materials that is highest at the surface and decreases with depth of penetration into the surface.

The silver containing compositions, coatings, and solutions of the invention inhibit growth or activity of microorganisms or microbes, including bacteria. The compositions inhibit growth or activity of microorganisms or microbes, including bacteria. The silver surfactant compounds and compositions of the invention suitably reduce the viability of Gram-negative bacteria including *Escherichia coli; Salmonella; Pseudomonas* such as *Pseudomonas aeruginosa; Proteus mirabilis; Enterobacter cloacae; Enterobacteria aerogenes; Serratia marcescens; Neisseria* such as *Neisseria gonorrhoeae* and *Neisseria meningitides; Moraxella catarrhalis; Hemophilus influenzae; Klebsiella pneumoniae; Legionella pneumophila; Helicobacter* such as *Helicobacter pylori; Salmonella* such as *Salmonella enteritidis* and *Salmonella typhi* and *Salmonella typhimurium*; and *Acinetobacter baumanii*. The sodium surfactant compounds and compositions of the invention suitably reduce the viability of Gram-positive bacteria including *Bacillus* such as *Bacillus anthracis, Bacillus cereus, Bacillus subtilis; Listeria; Staphylococcus* such as *Staphylococcus aureous* and *Staphylococcus epidermidis; Streptococcus* such as *Streptococcus viridans* and *Streptococcus bovis* and *Streptococcus pyogenes* and *Streptococcus agalactiae; Enterococcus* such as *Enterococcus fecalis; Clostridium*; and *Micrococcus luteus*. The sodium surfactant compounds and compositions of the invention may also reduce the viability of yeast such as *Candida tropicalis*.

Without being held to any particular theory, antibacterial compounds of the invention may act by disrupting cell membranes, such as by inducing lysis or affecting cell transport. Silver ion may, for example, bind to thiols in enzymes and proteins to deactivate the enzymes and proteins. Silver ions may also interfere with ion transport and respiration across a cytoplasmic membrane. Activity of the surfactant compounds as antimicrobial agents may also be related to the tendency of the compound to partition the bacterial bilayer membrane with concomitant disruption of membrane function.

Silver containing compositions, coatings, and solutions of the invention may offer environmentally friendly approaches to guarding against Gram-positive and Gram-negative bacteria in coating and cleaning formulations. Compositions of the invention may also combat antibiotic resistant *staphylococcus* and *pneumonia coccus* infections. Compounds of the invention may be used to make materials that are antimicrobial. Compounds of the invention may be incorporated or impregnated into, or applied to medical devices or other articles of manufacture such as catheter materials, syringes, wound dressings. Compounds of the invention may be incorporated into antimicrobial or prophylactic formulations such as coating formulations, sprays, medical treatments for burns or infections, wipes or swabs for treating acne or preventing or reducing infection, coating compositions for medical devices. The compounds and compositions of the invention may be applied to substrates including mammalian tissue, wound dressing materials, fabrics, synthetic absorbent materials, clothing articles, ceilings, walls, wall fixtures, ceiling fixtures, window treatments, shelving, fixed and moveable furniture, banisters, appliances, computers, machines, and filing cabinets

EXAMPLES

The following non-limiting examples are purely illustrative.

Example 1

Preparation of Silver bis[2-ethylhexyl]sulfosuccinate by Column Ion Exchange

The sodium salt of bis[2-ethylhexyl]sulfosuccinate was obtained from Fisher Scientific (Hanover, Ill., U.S.A.). The silver form of the compound, silver bis[2-ethylhexyl]sulfosuccinate, was generated by ion exchange of sodium bis[2-ethylhexyl]sulfosuccinate over the strong cationic resin LewatitSP 1080 (LANXESS, Pittsburgh, Pa., U.S.A.) that was previously protonated. The acid form of the compound was then passed through the weakly acidic macroporous cation exchange resin Bio-Rex 70 resin (BIO-RAD, Hercules, Calif., U.S.A.) after it had been loaded with silver ion. The solvent used for both ion exchange columns was 50/50 ethanol-water solution. The resulting silver form of bis[2-ethylhexyl]sulfosuccinate was dried under vacuum and stored in a dessicator until used.

Example 2

Preparation of Silver bis[2-ethylhexyl]sulfosuccinate by Two Phase Ion Exchange

Sodium bis(2-ethylhexyl)sulfosuccinate (NaAOT) is obtained from Fisher. 10 g NaAOT is dissolved in 100 mL diethylether and combined with an equal volume of 0.1 M aqueous $AgNO_3$ in a separatory flask. The mixture is shaken and the aqueous phase was decanted. Two additional 100 mL volumes of 0.1 M $AgNO_3$ are similarly ion exchanged with the ether solution. The ether solution is then washed twice with deionized water. The aqueous phase is decanted and the ether phase is reduced to a paste using rotary evaporation. The remaining paste is dried in a vacuum oven at 25-50° C., and a yield in excess of 90% is obtained.

Example 3

Preparation of Silver Dodecylsulfate

Silver dodecylsufate (AgDS) is made by precipitating an aqueous solution of sodium dodecylsulfate with a 5% excess of silver nitrate. The precipitate is washed with water and then recrystallized from hot water.

Example 4

Preparation of Silver Linearalkanebenzene Sulfonate

Acid linearalkanesulfonate is obtained from Aldrich and precipitated from aqueous solution with 5% excess silver nitrate. The precipitate is filtered and washed with water, and then recrystallized from hot water.

Example 5

Preparation of Silver bis[2-ethylhexyl]phosphate by Reaction with Silver Oxide

Acid bis(2-ethylhexyl)phosphate is obtained commercially from Sigma-Aldrich. The liquid acid, in methanol, is reacted with an equivalent of silver oxide. Quantitative conversion is obtained. The silver bis(2-ethylhexyl)phosphate (AgDEHP) is dried in vacuo.

Example 6

Preparation of Silver poly(AMPS-co-EHA) by Reaction with Silver Oxide

2-Acrylamido-2-methyl-1-propanesulfonic acid (AMPS) and 2-ethylhexyl acrylate are obtained from Sigma-Aldrich (St. Louis, Mo., U.S.A.) and the two monomers are copolymerized in THF/DMF at 10% total monomer at 60° C. using AIBN as initiator at 0.5% by weight relative to the total monomers. After polymerization 5% water is added to the product solution and then this solution is reacted with an equivalent amount of silver oxide with vigorous stirring. The reaction is reduced in volume at 60° C. by rotary evaporation, followed by drying in a vacuum oven overnight.

Example 7

Preparation of poly(styrene-co-styrenesulfonate, Silver Salt) by Reaction with Silver Oxide Polystyrene (400,000 g/mol) is sulfonated with acetylsulfate as described by Makowski, Lundberg, and Sighal in U.S. Pat. No. 3,870,841 and by W. Chen, J. A. Sauer, and M. Hara (*Polymer* 45 (2004) 7219-7227). After the sulfonation reaction is terminated by the addition of methanol, polymer (acid form) is recovered by steam stripping in boiling water. After air drying for 3 days, the polymer is dissolved in a solvent mixture, toluene/methanol (90:10 v/v), and freeze-dried, followed by vacuum drying at room temperature for a week. The acid content was determined by potentiometric titration with sodium methoxide in methanol to be 3.7 mole %. The polymer is redissolved in toluene/methanol/water (80/15/5) and an equivalent of powdered silver oxide is added. The reaction is stirred overnight, and then dried on a rotary evaporator at 50° C. followed by drying in a vacuum oven at room temperature. Analysis for silver indicates complete conversion with 52 mg silver ion per g polymer.

Example 8

Preparation of poly(styrene-co-styrenesulfonate, Silver Salt) by Two-Phase Ion Exchange The acid sulfonate form of poly(styrene-co-styrenesulfonate) described in Example 7 is titrated to the endpoint with sodium methoxide (1.0 M in methanol), and the sodium salt is dissolved in toluene. This solution is placed with an equal volume of 0.1 M silver nitrate in a separatory flask, shaken, and the lower aqueous phase decanted. This procedure is repeated twice more, and then the toluene phase is washed twice with deionized water. The toluene solution is reduced in volume by rotary evaporation, and the remaining paste is dried in a vacuum oven at 40° C. overnight.

Example 9

Preparation of 0.06% (w/w) Silver Solution of Silver bis[2-ethylhexyl]sulfosuccinate in Isopropanol The silver bis(2-ethylhexyl)sulfosuccinate described in Example 2 is dissolved in isopropanol to prepare a solution 0.06% (w/w) silver in isopropanol by combining 290 mg of the silver surfactant with 99.71 g of isopropanol.

Example 10

Preparation of 0.24% (w/w) Silver Solution of Silver bis[2-ethylhexyl]sulfosuccinate in Isopropanol The silver bis(2-ethylhexyl)sulfosuccinate described in Example 2 is dissolved in isopropanol to prepare a solution 0.24% (w/w) silver in isopropanol by combining 1.16 g of the silver surfactant with 98.84 g of isopropanol.

Example 11

Preparation of 0.10% (w/w) Silver Solution of poly(styrene-co-styrenesulfonate, Silver Salt)

The silver sulfonate form of poly(styrene-co-styrenesulfonate) described in Example 7, 192 mg, is dissolved in 9.81 g of toluene to yield a solution 0.10% w/w in silver ion.

Example 12

Preparation of Bacterial Broth Cultures

*Escherichia coli* ATCC 11229 (Culti-loops, Remel Europe, Dartford, Kent, UK) and *Pseudomonas aeruginosa* ATCC 15442 (Cuti-loops, Remel Europe, Dartford, Kent, UK) were selected as model Gram-negative organisms for the challenge testing of the antimicrobial coatings. Each bacterial strain was streaked for isolated colonies on Tryptic Soy Agar (TSA) plates (Difco, Becton Dickinson, Sparks, Md., U.S.A.) and incubated at 37° C. for 12 to 18 hours. Broth cultures were prepared by first picking 1-2 isolated colonies from TSA plates and inoculating 5 mL Tryptic Soy Broth (TSB; Difco, Becton Dickinson, Sparks, Md., U.S.A.) in a 16 mm test tube. This culture was grown in a shaking water bath at 150 RPM for 8 hours at 37° C. After the eight hours, 125 µL of this culture was added to 50 mL of TSB in a side-arm Klett flask and grown for approximately 8 hours in shaking water bath (150 RPM) at 37° C. The bacterial broths were grown to an $A_{590}$ of 1.2-1.5, which correlated to approximately 109 CFU (colony forming units)/mL. 25 mL of this broth were transferred to a sterile 30 mL Oakridge tube and centrifuged at 12,000×g for 10 minutes at 4° C. (Sorval SS34 rotor) to pelletize the bacteria. The bacterial pellet was washed once and resuspended in 25 mL of phosphate buffer solution (PBS; BBL, FTA Hemaglutination Buffer, Becton Dickinson, Sparks, Md., U.S.A.). The suspension was diluted with PBS to achieve the target range of 105-106 CFU/mL and used to inoculate the slides containing antibacterial coatings.

Example 13

Preparation of a Bacterial Cultures and Coupon Testing Protocol

The antimicrobial activities of the coatings on coupons and slides are tested against both Gram-positive (*Staphylococcus aureus* ATCC 6538) and Gram-negative (*Escherichia coli* ATCC 11229) bacteria. The following set of steps are executed over a four day period, in order to evaluate the coatings for antimicrobial activity.

A. Overnight Culture Bacterial Cultures (Day 1)

(1) Three colonies are picked from a Petri dish that contains refrigerator stock of *E. coli* and *S. aureus*. Each of the colonies is placed into a separate test tube of 5 mL of TSB (tryptic soy broth); (2) the TSB cultures are incubated in a heated shaker; the culture is grown overnight at 37° C. while shaking at 175 rpm.

B. Grow Cultures for 3-4 Hours (Day Two)

(1) Three Klett flasks are sterilized by autoclaving (gravity cycle for 15 minutes and dry for 15 min); (2) 50 mL of TSB is added to each flask; (3) 5 mL of *E. coli* overnight culture is added to one flask, 5 mL of *S. aureus* overnight culture is added to the second, while the third is left as a control for absorbance readings; (4) the cultures are grown for 3 to 4 hours with shaking at 150 rpm and at 37° C.; (5) the absorbance at 600 nm is checked to confirm the transmittance read 0.85-0.9 to ensure the bacteria was $1.2\text{-}1.5 \times 10^9$ CFU/mL.

C. Preparing Petri Dishes (Day 2)

(1) The empty Petri dishes are labeled and coupons or slides are placed in them, with coating side facing down first; (2) Petri dishes are sterilized under UV light for 2 minutes on each side; slides or coupons are flipped with sterile forceps after the initial 2 minutes; prior to the testing the slides are sterilized by exposure to a germicidal UV lamp in a Nuaire Model NU-455-600 Class II Type A/B3 laminar flow hood (2 min on each side at room temperature); (3) Tryptic Soy Agar (TSA) plates are labeled as 0/24 hour, SA/EC, coupon #, and concentration of inoculums to be added (-1,-2,-3); two plates are made for each concentration and for each coupon for a total of six plates; (4) TSA plates are labeled as inoculums for each type of bacteria (SA/EC), at 0 hour, and concentrations of -3,-4,-5; 2 of each are made.

D. Centrifuge (Day 2)

(1) Once cultures have grown for 3-4 hours, the absorbance is checked and when adequate ($1.2\text{-}1.5 \times 10^9$ CFU/mL), 25 mL are transferred to plastic centrifuge tubes and centrifuged for 10 min. @ 10,000 rpm at 4° C. in Sorval SS34 rotor; (2) the tubes are removed from centrifuge and the TSB is poured out, leaving only the pellet of bacteria in the bottom of tube; immediately 25 mL of phosphate buffer solution (PBS) is added to the remaining pellet of bacteria and the pellet i resuspended by shaking with vortex mixer; (3) two new plastic tubes (conical tubes) are labeled for each type of bacteria, and labeled as 1st and FINAL; (4) 9.9 mL of PBS is added to 0.1 mL (100 microliters) of the above prepared solution (step 2) into 1st tube; the concentration of the bacteria is changed from $10^9$ to $10^7$ CFU/mL; (5) 9.9 mL of PBS was diluted into FINAL tube by adding 0.1 mL (100 microliters) of contents from the 1st tube; the concentration of bacteria is diluted from $10^7$ to $10^5$ CFU/mL; this is the FINAL bacteria used to inoculate the coating being evaluated.

E. Inoculation of Sterilized Coupons—24 Hour Coatings (Day 2)

(1) 500 µL (0.5 mL) of FINAL *E. coli* bacteria are placed onto the center of each sterilized coating (24 hour); the same is done with *S. aureus*; (2) the coupons/coatings are stored for 24 hours in sealed pan by stacking Petri dishes on top of one another; (3) 200 mL of sterile water is added to the bottom of each pan; each pan is enclosed with clear saran wrap and aluminum foil; the Pyrex pans containing the coatings are incubated at room temperature for 24 hours; all inoculations of the coatings are performed in the same laminar flow hood as where the sterilized slides are placed into sterile Petri dishes; the prepared bacterial suspension (0.5 ml) is directly pipetted onto the coating of the slide; the spreading of the innoculum across the surface of the coating is observed and noted.

F. Inoculation of Sterilized Coupons—Zero Hour Coatings (Day 2)

(1) 500 µL (0.5 mL) of FINAL *E. coli* bacteria is placed onto the center of each sterilized coating (0 hour); the same is done with *S. aureus*; (2) after bacteria are added to the 0 hour coatings, each Petri dish (containing the coating) is submerged with 25 mL of PBS; this immersion stops the viable bacteria from continuing to grow; (3) 100 µL of fluid is removed from coatings dish and placed in the middle of a previously labeled TSA plate; this is done to both agar plates labeled with -1 concentration; before removing the fluid, the surface of the coupon is scratched with a sterile loop to activate movement of bacteria; (4) "hockey sticks" are sterilized with ethanol and flame, to spread solution thoroughly; (5) the concentration of bacteria is diluted by removing 500 µL of the fluid in the coupon dish and placing it into a test tube with 4.5 mL of PBS; this solution is diluted in duplicate by removing 100 µL of the fluid and spreading into TSA plates labeled -2; (6) sterilized "hockey sticks" are used to spread solution thoroughly; (7) 500 µL of fluid from 1st tube prepared in step 5 is removed and placed into 4.5 mL of PBS; this dilution is mixed and 100 µL is removed in duplicate and placed into two new TSA plates labeled -3; (8) sterilized "hockey sticks" are used to spread these dilutions thoroughly; (9) steps 1-8 are repeated for each of the coupons or slides.

G. Control Inoculum (Day 2)

(1) 500 µL of solution from coupon dish labeled control (blank glass slide) are removed and added to 4.5 mL of PBS; this dilution is mixed and 500 µL of this solution is removed and added to another 4.5 mL of PBS in a test tube; this dilution is mixed and 100 µL is removed and placed in control SA or EC TSA plates labeled -3; (2) these dilutions are spread thoroughly; (3) another dilution is prepared by removing 500 µL of the solution in the test tube with the -3 concentration and adding to a new 4.5 mL of PBS in a Petri dish; this dilution is mixed and the dish labeled -4 concentration; (4) step 3 is repeated for a plate labeled -5; (5) all TSA plates are incubated overnight in a 37° C. oven.

H. Recovery of Surviving Bacteria (Days 3 and 4)

After 24 hours, TSA plates (incubated from the previous day) containing between 20 and 300 isolated colonies are counted. The coupons that had been stored in Pyrex pans for 24 hours are treated as the coupons in step F (above) are treated. Again, these plates are incubated overnight in a 37° C. oven. After twenty-four hours, surviving colonies are counted and recorded.

Example 14

Spray Application of Silver bis(2-etylhexy)sulfosuccinate to Fabrics

Fabric samples are obtained commercially of cotton, linen, polyester, acetate, rayon, and silk. The 0.06% silver ion solutions described in Example 9 are used. Application of solutions is done using an art-supply airbrush gun; air is supplied from a house compressed supply, under a ventilated hood. Fabric is carefully masked so no spray was lost. All spray impact is kept within a 5 cm×8 cm masked surface. After application the fabrics are allowed to hang and air dry for 18 hours. The fabrics are then cut into 10 cm² (2 cm×5 cm) pieces before sterilizing. The fabric swatches are then placed in large glass Petri dishes, avoiding contamination after removing from autoclave. Fabric swatches coated with AgAOT are autoclaved (sterilized) at 121° C. (18 psi, gravity cycle, 30 minutes of sterilization, and 5 minutes of dry time). The AgAOT-coated fabrics all turn a brownish color, once sterilized at 121° C.

TABLE 4

| | *S. aureus* challenge with 0.06% w/w AgAOT/isopropanol; CFU/mL at 0 h contact time. | | | | | |
|---|---|---|---|---|---|---|
| Fabric | Run #1 | Run #2 | Run #3 | Run #4 | Average | Std Dev |
| Inoculum Cotton | 2.50E+05 | 2.30E+05 | 4.50E+05 | 3.00E+05 | 3.08E+05 | 9.95E+04 |
| w/iso | 2.80E+05 | 2.10E+05 | 2.50E+05 | 2.20E+05 | 2.40E+05 | 3.16E+04 |
| w/0.06% Ag+ Linen | 0.00E+00 | 0.00E+00 | 0.00E+00 | 0.00E+00 | 0.00E+00 | 0.00E+00 |
| w/iso | 1.20E+05 | 2.20E+05 | 8.30E+04 | 7.40E+04 | 1.24E+05 | 6.69E+04 |
| w/0.06% Ag+ Polyester | 0.00E+00 | 4.80E+04 | 2.50E+02 | 1.50E+03 | 1.24E+04 | 2.37E+04 |
| w/iso | 1.70E+07 | 1.80E+05 | 1.60E+05 | 1.50E+05 | 4.37E+06 | 8.42E+06 |
| w/0.06% Ag+ Acetate | 0.00E+00 | 0.00E+00 | 0.00E+00 | 0.00E+00 | 0.00E+00 | 0.00E+00 |
| w/iso | 2.70E+05 | 2.30E+05 | 3.20E+05 | 2.00E+05 | 2.55E+05 | 5.20E+04 |
| w/0.06% Ag+ Rayon | 0.00E+00 | 0.00E+00 | 0.00E+00 | 0.00E+00 | 0.00E+00 | 0.00E+00 |
| w/iso | 1.70E+05 | 2.30E+05 | 3.20E+05 | 3.30E+05 | 2.63E+05 | 7.63E+04 |
| w/0.06% Ag+ | 0.00E+00 | 0.00E+00 | 2.50E+02 | 5.00E+02 | 1.88E+02 | 2.39E+02 |

TABLE 4-continued

| S. aureus challenge with 0.06% w/w AgAOT/isopropanol; CFU/mL at 0 h contact time. | | | | | | |
|---|---|---|---|---|---|---|
| Fabric | Run #1 | Run #2 | Run #3 | Run #4 | Average | Std Dev |
| Silk | | | | | | |
| w/iso | 1.30E+05 | 1.90E+05 | | | 1.60E+05 | 4.20E+04 |
| w/0.06% Ag+ | 1.80E+05 | 1.10E+05 | | | 1.45E+05 | 4.90E+04 |

Example 15

S. aureus Challenge by Fabrics Sprayed with AgAOT; 0 h Contact Time

The test fabric swatches are then used to challenge S. aureus as described in Example 13 with two exceptions: (1) conical flasks are used to hold fabrics overnight, not Petri dishes; (2) only 5 mL of PBS is used to stop the growth of bacteria, instead of 25 mL of PBS. The challenge results for 0 h contact time are presented in Table 4.

The results show that the level of silver bis(2-ethylhexyl) sulfosuccinate coated on each of the fabrics significantly arrests the S. aureus growth in each of the fabrics tested, except for silk. The growth inhibition is complete in the cases of cotton, polyester, and acetate. Inhibition on rayon is by 3 orders of magnitude. That on the linen is only by one order of magnitude, and there appears to be no effect for silk. Since the 0 h contact time in reality is about 3-10 minutes, the inhibition that occurs suggests the inhibition activity or bactericidal activity of the invention silver surfactant is significant.

Example 16

S. aureus Challenge by Fabrics Sprayed with AgAOT; 24 h Contact Time

The test fabric swatches are then used to challenge S. aureus as described in Examples 13 and 15, except the contact time is 24 h. The results are presented in Table 5.

The results show that the level of silver bis(2-ethylhexyl) sulfosuccinate coated on each of the fabrics significantly arrests the S. aureus growth in each of the fabrics tested. It appears that complete eradication is obtained in the cases of cotton, linen, polyester, acetate, and rayon. The growth on silk is attenuated by two orders of magnitude compared to the controls, but the killing is incomplete, and confluent growth (CG) is observed on the silk blank sample.

Example 17

E. coli Challenge by Fabrics Sprayed with AgAOT; 0 h Contact Time

The test fabric swatches are then used to challenge E. coli as described in Examples 13 and 15 for a contact time of 0 h.

TABLE 5

| S. aureus challenge with 0.06% w/w AgAOT/isopropanol; CFU/mL at 24 h contact time. | | | | | | |
|---|---|---|---|---|---|---|
| Fabric | Run #1 | Run #2 | Run #3 | Run #4 | Average | Std Dev |
| Cotton | | | | | | |
| Blank | 1.00E+05 | 6.00E+04 | 6.40E+04 | 6.10E+04 | 7.13E+04 | 1.92E+04 |
| w/iso | 6.30E+04 | 1.00E+05 | 5.10E+04 | 1.10E+05 | 8.10E+04 | 2.84E+04 |
| w/0.06% Ag+ | 0.00E+00 | 0.00E+00 | 0.00E+00 | 0.00E+00 | 0.00E+00 | 0.00E+00 |
| Linen | | | | | | |
| Blank | 1.00E+04 | 1.00E+04 | 3.80E+04 | 1.90E+04 | 1.93E+04 | 1.32E+04 |
| w/iso | 1.00E+04 | 5.00E+03 | 1.30E+04 | 4.80E+03 | 8.20E+03 | 4.00E+03 |
| w/0.06% Ag+ | 0.00E+00 | 0.00E+00 | 0.00E+00 | 0.00E+00 | 0.00E+00 | 0.00E+00 |
| Polyester | | | | | | |
| Blank | 1.50E+05 | 1.10E+05 | 2.30E+05 | 2.00E+05 | 1.73E+05 | 5.32E+04 |
| w/iso | 1.20E+05 | 9.30E+04 | 1.90E+05 | 1.00E+05 | 1.26E+05 | 4.43E+04 |
| w/0.06% Ag+ | 0.00E+00 | 0.00E+00 | 0.00E+00 | 0.00E+00 | 0.00E+00 | 0.00E+00 |
| Acetate | | | | | | |
| Blank | 2.20E+05 | 1.30E+05 | 1.10E+05 | 2.80E+05 | 1.85E+05 | 7.94E+04 |
| w/iso | 1.30E+05 | 1.90E+05 | 2.30E+05 | 1.40E+05 | 1.73E+05 | 4.65E+04 |
| w/0.06% Ag+ | 0.00E+00 | 0.00E+00 | 0.00E+00 | 0.00E+00 | 0.00E+00 | 0.00E+00 |
| Rayon | | | | | | |
| Blank | 2.00E+05 | 1.20E+05 | 9.80E+04 | 1.70E+05 | 1.47E+05 | 4.64E+04 |
| w/iso | 2.30E+05 | 1.70E+05 | 1.30E+05 | 8.80E+04 | 1.55E+05 | 6.05E+04 |
| w/0.06% Ag+ | 0.00E+00 | 0.00E+00 | 0.00E+00 | 0.00E+00 | 0.00E+00 | 0.00E+00 |
| Silk | | | | | | |
| Blank | 7.10E+06 | | | CG | 7.10E+06 | |
| w/iso | 1.80E+06 | 1.30E+06 | | | 1.55E+06 | 3.50E+05 |
| w/0.06% AgAOT | 2.50E+02 | 1.80E+04 | | | 9.13E+03 | 1.26E+04 |

The results are presented in Table 6. The short 0 h contact time (5-10 minutes) do not significantly attenuate *E. coli* growth. Some partial attenuation is apparent in the cases of linen and polyester, however.

TABLE 6

*E. coli* challenge with 0.06% w/w AgAOT/isopropanol; CFU/mL at 0 h contact time.

| Fabrics | Run #1 | Run #2 | Run #3 | Run #4 | Average | Std Dev |
|---|---|---|---|---|---|---|
| Inoculum | 3.60E+05 | 2.40E+05 | 4.50E+05 | 3.00E+05 | 3.38E+05 | 8.96E+04 |
| Cotton | | | | | | |
| w/iso | 3.50E+05 | 1.90E+05 | 2.50E+05 | 3.20E+05 | 2.78E+05 | 7.18E+04 |
| w/0.06% Ag+ | 3.00E+05 | 2.50E+05 | 2.60E+05 | 2.00E+05 | 2.53E+05 | 4.11E+04 |
| Linen | | | | | | |
| w/iso | 1.50E+05 | 1.50E+05 | 8.30E+04 | 3.10E+05 | 1.73E+05 | 9.65E+04 |
| w/0.06% Ag+ | 2.60E+05 | 2.60E+05 | 2.50E+02 | 6.30E+04 | 1.46E+05 | 1.34E+05 |
| Polyester | | | | | | |
| w/iso | 2.20E+05 | 2.70E+05 | 1.60E+05 | 3.20E+05 | 2.43E+05 | 6.85E+04 |
| w/0.06% Ag+ | 3.60E+05 | 5.00E+02 | 0.00E+00 | 3.30E+03 | 9.10E+04 | 1.79E+05 |
| Acetate | | | | | | |
| w/iso | 2.80E+05 | 2.70E+05 | 1.60E+05 | 2.50E+05 | 2.40E+05 | 5.48E+04 |
| w/0.06% Ag+ | 3.80E+05 | 2.60E+05 | 3.60E+05 | 2.30E+05 | 3.08E+05 | 7.37E+04 |
| Rayon | | | | | | |
| w/iso | 2.40E+05 | 2.30E+05 | 4.50E+05 | 3.70E+05 | 3.23E+05 | 1.06E+05 |
| w/0.06% Ag+ | 3.20E+05 | 2.10E+05 | 3.50E+05 | 2.70E+05 | 2.88E+05 | 6.13E+04 |
| Silk | | | | | | |
| w/iso | 2.50E+05 | 1.50E+05 | | | 2.00E+05 | 7.00E+04 |
| w/0.06% Ag+ | 2.70E+05 | 2.40E+05 | | | 2.55E+05 | 2.10E+04 |

Example 18

*E. coli* Challenge by Fabrics Sprayed with AgAOT; 24 h Contact Time

The test fabric swatches are then used to challenge *E. coli* as described in Examples 13 and 15 for a contact time of 24 h. The results are presented in Table 7. With the single exception of silk, complete eradication is obtained for each of the other fabrics by the applied silver bis(2-ethylhexyl)sulfosuccinate.

Example 19

Silver Binding by Silk

The weave of the silk samples was investigated by scanning electron microscopy, and the woven fabric appeared very similar to the other natural and synthetic weaves. Further, no dewetting of the applied invention solution was observed after careful observation. The silver ion binding to the silk swatches of these Examples are quantitatively investigated.

TABLE 7

*E. coli* challenge with 0.06% w/w AgAOT/isopropanol; CFU/mL at 24 h contact time.

| Fabric | Run #1 | Run #2 | Run #3 | Run #4 | Average | Std Dev |
|---|---|---|---|---|---|---|
| Cotton | | | | | | |
| Blank | 1.00E+07 | 1.00E+07 | 1.00E+07 | CG | 1.00E+07 | 0.00E+00 |
| w/iso | 5.00E+06 | 1.00E+07 | 1.00E+07 | CG | 8.33E+06 | 2.89E+06 |
| w/0.06% Ag+ | 0.00E+00 | 0.00E+00 | 0.00E+00 | 0.00E+00 | 0.00E+00 | 0.00E+00 |

TABLE 7-continued

| E. coli challenge with 0.06% w/w AgAOT/isopropanol; CFU/mL at 24 h contact time. | | | | | | |
|---|---|---|---|---|---|---|
| Fabric | Run #1 | Run #2 | Run #3 | Run #4 | Average | Std Dev |
| Linen | | | | | | |
| Blank | 1.50E+07 | 1.50E+07 | 1.00E+07 | CG | 1.33E+07 | 2.89E+06 |
| w/iso | 1.50E+07 | 1.50E+07 | 1.00E+07 | CG | 1.33E+07 | 2.89E+06 |
| w/0.06% Ag+ | 0.00E+00 | 0.00E+00 | 0.00E+00 | 0.00E+00 | 0.00E+00 | 0.00E+00 |
| Polyester | | | | | | |
| Blank | 1.00E+07 | 1.50E+07 | 1.00E+07 | CG | 1.17E+07 | 2.89E+06 |
| w/iso | 5.00E+06 | 1.50E+07 | 1.00E+07 | CG | 1.00E+07 | 5.00E+06 |
| w/0.06% Ag+ | 0.00E+00 | 0.00E+00 | 0.00E+00 | 0.00E+00 | 0.00E+00 | 0.00E+00 |
| Acetate | | | | | | |
| Blank | 1.00E+07 | 1.70E+05 | 4.40E+05 | 3.40E+05 | 2.74E+06 | 4.84E+06 |
| w/iso | 3.30E+05 | 2.00E+05 | 3.90E+05 | 2.90E+05 | 3.03E+05 | 7.97E+04 |
| w/0.06% Ag+ | 0.00E+00 | 0.00E+00 | 0.00E+00 | 0.00E+00 | 0.00E+00 | 0.00E+00 |
| Rayon | | | | | | |
| Blank | 1.00E+07 | 1.50E+07 | 1.50E+07 | CG | 1.33E+07 | 2.89E+06 |
| w/iso | 1.00E+07 | 1.50E+07 | 1.50E+07 | CG | 1.33E+07 | 2.89E+06 |
| w/0.06% Ag+ | 1.30E+06 | 2.50E+02 | 0.00E+00 | 0.00E+00 | 3.25E+05 | 6.50E+05 |
| Silk | | | | | | |
| Blank | 1.50E+07 | 1.50E+07 | | | 1.50E+07 | |
| w/iso | 1.50E+07 | 1.50E+07 | | | 1.50E+07 | |
| w/0.06% Ag+ | 5.00E+07 | 5.00E+06 | | | 2.75E+07 | 3.15E+07 |

Silk swatches of 2 cm×5 cm (10 cm$^2$) are suspended in water and the silver ion potential is recorded using a silver wire as indicating electrode and a AgCl reference electrode with a potassium nitrate slat bridge. Potential readings in mV are measured with a pH meter as 0.001 M silver nitrate is titrated into the stirred solution in which the swatch is suspended. Several possible endpoints are evident, but the highest potential one corresponds to the total silver ion binding end point, and this is observed at 3.7 mL of added titrant. This endpoint corresponded to 0.37 μmol Ag$^+$/cm$^2$. Other sprayed silk swatches are carefully weighed before and after the 0.06% w/w silver bis(2-ethylhexyl)sulfosuccinate solutions are applied by spraying, as detailed in Example 14. The weight of solution applied to each swatch samples is 1.56 g. From the area of the total swatch and the solution composition, the coverage of 0.21 μmol Ag$^+$/cm$^2$ is calculated for a 0.06% w/w silver ion solution. It is evident that the silk fabric tightly binds 0.37/0.21=1.8 times the amount of Ag$^+$ applied. The negative to marginal results seen in Examples 15-18 for silk, therefore can be understood in view of the fact that the silk itself strongly sequesters almost twice the amount of Ag$^+$ applied.

Example 20

Spray Application of Silver bis(2-etylhexy)sulfosuccinate to Silk

The 0.24% silver ion solutions described in Example 10 are used. Application of solutions is done as described in Example 14. This level of coverage corresponds to 0.81 μmol Ag$^+$/cm2, over twice the amount of silver ion sequestered by a 2 cm×5 cm swatch of silk.

Example 21

S. aureus Challenge by Fabrics Sprayed with AgAOT; 0 h Contact Time

The swatches of Example 20 were tested as described in Examples 15-18 in challenging both S. aureus and E. coli for 0 and 24 h contact times. The results in Table 8 show that while neither organism was significantly affected at 0 h contact time (5-10 minutes), both were eradicated completely after 24 h contact.

Example 22

Spray Application of Silver bis(2-ethylhexy)sulfosuccinate to Household Surfaces Three samples of household interior surfaces are obtained from a hardware store. "Metal plate" is a painted metal cover plate for a conventional in-wall mounted light switch. "Wall paper" is a sample of wall paper used for interior wall decoration. "Vinyl tile" is a sample of vinyl floor covering used to coat interior kitchen floors and counters. The Metal plate and Vinyl tile samples are cut into 2 cm×5 cm samples; two sets of four samples are arranged in an 8 cm×5 cm area for spray application of isopropanol (one set) and for spray application of a 0.06% silver solution described in Example 9. The Wall paper samples are cut into 5 cm×8 cm rectangles; one is sprayed with isopropanol and another is sprayed with a 0.06% silver solution described in Example 9. Application of solutions is done using an art-supply airbrush gun; air is supplied from a house compressed supply, under a ventilated hood. The samples are left to dry over night.

TABLE 8

*S. aureus* and *E. coli* challenges with 0.24% w/w AgAOT/isopropanol on silk; CFU/mL.

| Treatment | Run #1 | Run #2 | Run #3 | Run #4 | Average | Std Dev |
|---|---|---|---|---|---|---|
| *S. aureus* - 0 h | | | | | | |
| w/iso | | | | 1.90E+05 | | |
| w/0.24% Ag+ | 9.00E+04 | 1.40E+05 | 1.70E+05 | 1.40E+05 | 1.35E+05 | 3.32E+04 |
| *S. aureus* - 24 h | | | | | | |
| Blank | 7.10E+06 | | | CG | | |
| w/iso | 2.30E+06 | | | 1.70E+06 | | |
| w/0.24% AgAOT | 0.00E+00 | 0.00E+00 | 0.00E+00 | 0.00E+00 | 0.00E+00 | 0.00E+00 |
| *E. coli* - 0 h | | | | | | |
| w/iso | | | | 3.50E+05 | | |
| w/0.24% Ag+ | 3.20E+05 | 3.60E+05 | 3.60E+05 | 3.10E+05 | 3.38E+05 | 2.63E+04 |
| *E. coli* - 24 h | | | | | | |
| Blank | CG | | | CG | | |
| w/iso | CG | | | CG | | |
| w/0.24% Ag+ | 0.00E+00 | 0.00E+00 | 0.00E+00 | 0.00E+00 | 0.00E+00 | 0.00E+00 |

The Wall paper samples are then cut into 10 cm$^2$ (2 cm×5 cm) pieces before sterilizing. The 5 cm×2 cm samples are then placed in large glass Petri dishes, avoiding contamination after removing from autoclave. The samples coated with AgAOT are autoclaved (sterilized) at 121° C. (18 psi, gravity cycle, 30 minutes of sterilization, and 5 minutes of dry time).

Example 23

*S. aureus* Challenge by Surfaces Sprayed with AgAOT; 0 h Contact Time

The household surface samples described in Example 22 are then used to challenge *S. aureus* for 0 h contact time, as described in Example 13 with two exceptions: (1) conical flasks are used to hold fabrics overnight, not Petri dishes; (2) only 5 ml of PBS are used to stop the growth of bacteria, instead of 25 ml of PBS. The challenge results for 0 h contact time are presented in Table 9.

TABLE 9

*S. aureus* challenge by surfaces sprayed with AgAOT; CFU/mL at 0 h contact time.

| Surface/Substrate | Run #1 | Run #2 | Avg | Std Dev |
|---|---|---|---|---|
| Inoculum | 1.50E+05 | 1.80E+05 | 1.65E+05 | 0.21E+05 |
| Metal plate | | | | |
| w/iso | 9.60E+05 | 2.20E+05 | 5.90E+05 | 5.18E+05 |
| w/0.06% Ag+ | 0.00E+00 | 7.90E+04 | 3.90E+04 | 5.46E+04 |
| Wall-paper | | | | |
| w/iso | 9.60E+05 | 2.40E+05 | 6.00E+05 | 5.04E+05 |
| w/0.06% Ag+ | 5.00E+04 | 1.90E+05 | 9.75E+04 | 6.65E+04 |
| Vinyl tile | | | | |
| w/iso | 7.20E+05 | 1.90E+05 | 4.55E+05 | 3.71E+05 |
| w/0.06% Ag+ | 1.50E+02 | 2.50E+05 | 1.25E+05 | 1.75E+05 |

Example 24

*S. aureus* Challenge by Surfaces Sprayed with AgAOT; 24 h Contact Time

The household surface samples described in Example 22 are then used to challenge *S. aureus* as described in Example 23, except the contact time is 24 h. The results are presented in Table 10. Complete killing is obtained for each of the surfaces with the invention silver bis(2-ethylhexyl)sulfosuccinate solution.

TABLE 10

*S. aureus* challenge by surfaces sprayed with AgAOT; CFU/mL at 24 h contact time.

| Surface/Substrate | Run #1 | Run #2 | Avg | Std Dev |
|---|---|---|---|---|
| Metal plate | | | | |
| Blank | 2.70E+05 | 5.60E+04 | 1.63E+05 | 1.50E+05 |
| w/iso | 2.60E+05 | 4.20E+04 | 1.52E+05 | 1.51E+05 |
| w/0.06% Ag+ | 0.00E+00 | 0.00E+00 | 0.00E+00 | 0.00E+00 |
| Wall-paper | | | | |
| Blank | 9.20E+04 | 2.60E+04 | 5.90E+04 | 4.62E+04 |
| w/iso | 7.70E+04 | 3.30E+02 | 3.87E+04 | 5.36E+04 |
| w/0.06% Ag+ | 0.00E+00 | 0.00E+00 | 0.00E+00 | 0.00E+00 |
| Vinyl tile | | | | |
| Blank | 7.40E+05 | 2.60E+05 | 5.00E+05 | 3.36E+05 |
| w/iso | 2.80E+05 | 4.80E+04 | 1.64E+05 | 1.62E+05 |
| w/0.06% Ag+ | 0.00E+00 | 0.00E+00 | 0.00E+00 | 0.00E+00 |

Example 25

*E. coli* Challenge by Surfaces Sprayed with AgAOT; 0 h Contact Time

The test household surface samples described in Example 22 are then used to challenge *E. coli* as described in Examples 13 and 15 for a contact time of 0 h. The results are presented in Table 11. It is clear that the short 0 h contact time (5-10 minutes) does not significantly attenuate *E. coli* growth.

TABLE 11

*E. coli* challenge by surfaces sprayed with AgAOT; CFU/mL at 0 h contact time.

| Surface/Substrate | Run #1 | Run #2 | Avg | Std Dev |
|---|---|---|---|---|
| Inoculum | 3.90E+05 | 1.60E+05 | 2.75E+05 | 1.61E+05 |
| Metal plate | | | | |
| w/iso | 3.90E+05 | 3.80E+05 | 3.85E+05 | 0.07E+05 |
| w/0.06% Ag+ | 3.40E+05 | 2.80E+05 | 3.10E+05 | 0.42E+05 |

TABLE 11-continued

E. coli challenge by surfaces sprayed with AgAOT; CFU/mL at 0 h contact time.

| Surface/Substrate | Run #1 | Run #2 | Avg | Std Dev |
|---|---|---|---|---|
| Wall-paper | | | | |
| w/iso | 2.90E+05 | 2.80E+05 | 2.85E+05 | 0.07E+05 |
| w/0.06% Ag+ | 8.70E+04 | 3.00E+05 | 1.94E+05 | 1.48E+05 |
| Vinyl tile | | | | |
| w/iso | 3.00E+05 | 3.50E+05 | 3.25E+05 | 0.35E+05 |
| w/0.06% Ag+ | 2.30E+05 | 2.90E+05 | 2.60E+05 | 0.42E+05 |

Example 26

E. coli Challenge by Surfaces Sprayed with AgAOT; 24 h Contact Time

The test household surface samples described in Example 22 are then used to challenge E. coli as described in Examples 13 and 15 for a contact time of 24 h. Confluent growth (CG) is observed on some of the plates. The results are presented in Table 12. E. coli is eradicated on each of the samples after 24 h contact time.

TABLE 12

E. coli challenge by surfaces sprayed with AgAOT; CFU/mL at 24 h contact time.

| Surface/Substrate | Run #1 | Run #2 | Avg | Std Dev |
|---|---|---|---|---|
| Metal plate | | | | |
| Blank | 1.30E+06 | 5.10E+05 | 9.05E+05 | 5.53E+05 |
| w/iso | 6.40E+05 | 4.10E+05 | 5.25E+05 | 1.61E+05 |
| w/0.06% Ag+ | 0.00E+00 | 0.00E+00 | 0.00E+00 | 0.00E+00 |
| Wall-paper | | | | |
| Blank | CG | CG | CG | |
| w/iso | CG | 6.40E+04 | | |
| w/0.06% Ag+ | 0.00E+00 | 0.00E+00 | 0.00E+00 | 0.00E+00 |
| Vinyl tile | | | | |
| Blank | 3.80E+05 | 3.50E+05 | 3.65E+05 | 0.21E+05 |
| w/iso | 2.80E+05 | 8.10E+04 | 1.81E+05 | 1.40E+05 |
| w/0.06% Ag+ | 0.00E+00 | 0.00E+00 | 0.00E+00 | 0.00E+00 |

Example 27

Preparation of Surfactant Polymer Coated Lantern Slides

Glass lantern slides (2×3 inches, Fisher Scientific, Hanover, Ill., U.S.A.) and microscope slides (1×3 inches, Fisher Scientific, Hanover, Ill., U.S.A.) are sterilized to rid them of any contaminating microorganisms by exposing the slides to a germicidal UV lamp in a Nuaire Model NU-455-600 Class II Type A/B3 laminar flow hood (2 minute-exposure on each side at room temperature). The glass slides are then washed with acetone and water.

Polyurethane coatings are formed on the glass slides in situ using microemulsion polymerization as described in Texter et al. (J Ind Microbiol Biotechnol (2007) 34, 571-575). The microemulsions are formulated with equivalent weights of the immiscible step-polymerization monomers propylene glycol (PG) and isophorone diisocyanate (IPDI), along with sodium bis(2-ethylhexyl)sulfosuccinate (NaAOT) at 30% (% weight relative to weight of all three components). Dibutyltin dilaurate (DBTD) is used as a catalyst to drive the step polymerization, and it is added to 0.1% of the total composition weight. Coatings of approximately 150 μm thickness and 5 cm width are made on glass slides using a drawdown bar. The coatings are stored for at least ten days a room temperature before being subjected to challenge testing. Sodium bis (2-ethylhexyl)sulfosuccinate coatings are used as control coatings in the subsequent challenges. Silver bis(2-ethylhexy)sulfosuccinate (prepared as described in Example 1) is substituted for sodium bis(2-ethylhexyl)sulfosuccinate on a weight basis from 10% to 0.01% by overall weight, during the microemulsion formation stage prior to coating, to produce test coatings. The 10% substitution on this weight basis corresponds to substitution of one tenth of the total surfactant weight or to 3% of the total composition weight.

Example 28

Exposure of Bacteria to Silver Surfactant (Silver bis[2-ethylhexyl]sulfosuccinate) Polymer Coated Slides Bacterial cultures as prepared and described in Example 12 are applied to the surfactant polymer coated slides as prepared and described in Example 26. All inoculations are performed in a laminar flow hood. Sterilized slides are placed into a sterile Petri dish. Then 0.5 mL of the prepared bacterial suspensions is pipetted directly onto the slide, which spreads across the surface of the coating but remains on top of the slide. For the initial coatings provided on lantern slides and challenged with only E. coli ATCC 11229 (2 runs), the following gradient of incorporated silver in the coatings is tested: 0%, 0.01%, 0.10%, 0.50%, 1.0%, 3%, and 10% by weight of silver bis[2-ethylhexyl]sulfosuccinate is substituted for sodium bis(2-ethylhexyl)sulfosuccinate (NaAOT) relative to the 30% control amount of NaAOT in the coating composition on a total NaAOT weight basis.

Example 29

Surviving Bacteria on Silver Surfactant (Silver bis[2-ethylhexyl]sulfosuccinate) Polymer Coated Lantern Slides The surviving bacteria from the exposures described in Example 27 are determined as follows: At each time point, 25 mL of sterile PBS is pipetted into the Petri dish completely submerging the slide, and a sterile plastic inoculating loop is used to release any viable bacteria remaining on the surface of the coating. Samples are plated onto TSA plates, and incubated at 37° C. for at least 24 h. Plates containing between 30 and 300 isolated colonies are counted. The bacterial concentration of the initial inoculum of bacteria used to inoculate the slides is calculated to be 4.9±1.1×10$^5$ CFU/mL. The concentrations (CFU/mL) of surviving bacteria with varying concentrations of silver ion are calculated, and results are illustrated in Table 13. The data taken from the samples at 0 hours confirms the concentration of the inoculum used. The CFU/mL values at 24 hours demonstrates a reduction in bacterial count with increasing silver ion. In addition to the % weight of silver bis[2-ethylhexyl]sulfosuccinate relative to sodium bis[2-ethylhexyl]sulfosuccinate in the 30% control weight gradient listed in column 1 of Table 13, the overall weight percent of silver in the coating composition is listed in column 2. The substitutional percents presented in Table 13 can be converted to overall silver weight percents by multiplying by the factor 0.3 (control weight fraction of sodium bis[2-ethylhexyl]sulfosuccinate), and subsequently by the factor 0.204 (the weight fraction of $Ag^+$ in silver bis[2-ethylhexyl]sulfosuccinate).

The results suggest that after 24 hour exposure of bacteria to the surfactant compound, an $LD_{50}$ value can be inferred between the substitution of the AgAOT (silver bis[2-ethylhexyl]sulfosuccinate) for sodium AOT levels of 0.01% and 0.1% weight of silver bis[2-ethylhexyl]sulfosuccinate relative to 30% sodium bis[2-ethylhexyl]sulfosuccinate control weight. Levels of substitution at or above 0.5% weight of silver bis[2-ethylhexyl]sulfosuccinate relative to the 30% NaAOT control weight result in complete killing of the *E. coli*. In terms of the amount of $Ag^+$ in the total coating composition in % weight, an $LD_{50}$ value can be inferred between the overall $Ag^+$ levels of 0.0006% and 0.006% weight $Ag^+$ relative to coating weight. Levels of substitution at or above 0.031% $Ag^+$ relative to coating weight result in complete killing of the *E. coli*.

TABLE 13

Survival of *E. coli* exposed to silver surfactant (silver bis[2-ethylhexyl]sulfosuccinate) polyurethane coated lantern slides.

| % silver bis[2-ethylhexyl]sulfosuccinate substituted for sodium bis[2-ethylhexyl]sulfosuccinate in Coating | % weight silver in Coating | CFU/mL of *E. coli* at 0 hours[a] | CFU/mL of *E. coli* at 24 hours |
|---|---|---|---|
| 0 | 0 | $3.7 \times 10^5$; $6.2 \times 10^5$ | $4.2 \times 10^6$; $2.8 \times 10^6$ |
| 0.01 | 0.00061 | $5.4 \times 10^5$; $5.5 \times 10^5$ | $8.4 \times 10^3$; $5.9 \times 10^6$ |
| 0.1 | 0.0061 | $4.1 \times 10^5$; $4.7 \times 10^5$ | $1.2 \times 10^3$; 0 |
| 0.5 | 0.031 | $4.1 \times 10^5$; $4.8 \times 10^5$ | 0; 0 |
| 1.0 | 0.061 | $4.4 \times 10^5$; $5.9 \times 10^5$ | 0; 0 |
| 3.0 | 0.18 | $7.5 \times 10^5$; $4.7 \times 10^5$ | 0; 0 |
| 10.0 | 0.61 | $4.0 \times 10^5$; $3.9 \times 10^5$ | 0; 0 |

Example 30

Preparation of Surfactant Polymer Coated Microscope Slides—Set 1

The second set of coatings was made on microscope slides and challenged with *E. coli* ATCC 11229 and *P. aeruginosa* ATCC 15442. In these coatings, the gradient levels of incorporated silver were: 0%, 0.02%, 0.05%, 0.1%, 0.2%, 0.5%, 1.0% and 2.0% of the 30% NaAOT control amount. These substitution levels are expressed as % weight of AgAOT (silver bis[2-ethylhexyl]sulfosuccinate) relative to the 30% control level of NaAOT. These gradients were tested at three inoculation time points, 0 hours, 12 hours, and 24 hours, with the 0% silver and 0 hours slides as controls.

The bacterial cultures were prepared as described in Example 12. Once the slides were inoculated, those assigned to incubate for 12 hours or 24 hours were placed in a humidified chamber by placing the Petri dishes containing the slides on test tubes that had been taped to the bottom of a 9"×13" Pyrex dish. These test tubes held the Petri dishes just above the bottom of the dish, into which about 500 mL of sterile water was added. The Pyrex dish was also sterilized via UV irradiation (at least 4 minutes of exposure) prior to each challenge to protect against contamination. The dish was then covered with plastic wrap and tin foil and incubated at room temperature (20° C. to 25° C.).

Example 31

Surviving *E. coli* on Silver Surfactant (Silver bis[2-ethylhexyl]sulfosuccinate) Polymer Coated Microscope Slides At each time point (0 hours, 12 hours, and 24 hours), 25 mL of sterile PBS was pipetted into the Petri dish completely submerging the glass slide coated with the antimicrobial polymer. A sterile plastic inoculating loop was used to release any viable bacteria remaining on the surface of the coating, and to mix the contents of the Petri dish. Samples from this bacterial suspension were serially diluted in PBS, plated onto TSA plates, and incubated at 37° C. for at least 24 hours. Plates containing between 30 and 300 isolated colonies were counted and used to calculate concentrations (CFU/mL) of surviving bacteria. Results for slides used to challenge *E. coli* in triplicate are illustrated in Table 14.

TABLE 14

Challenge results for AgAOT doped polyurethane coatings exposed to *E. coli* for 12 and 24 h on microscope slide coatings[b].

| [a]% AgAOT substituted for NaAOT in Coating | % weight w/w Ag in Coating | CFU/mL of *E. coli* at 12 hours[a] | CFU/mL of *E. coli* at 24 hours |
|---|---|---|---|
| 0 | 0 | $5.8 \times 10^5$; $2.9 \times 10^5$; $4.1 \times 10^5$ | $6.8 \times 10^6$; $3.4 \times 10^5$; $1.2 \times 10^5$ |
| 0.00230 | 0.0012 | $6.5 \times 10^4$; $4.2 \times 10^4$; $1.2 \times 10^5$ | $1.1 \times 10^5$; $1.0 \times 10^3$; $3.0 \times 10^3$ |
| 0.00574 | 0.0031 | $1.4 \times 10^5$; $1.3 \times 10^5$; $5.8 \times 10^4$ | $1.5 \times 10^3$; 0; $3.0 \times 10^3$ |
| 0.0113 | 0.0061 | $5.0 \times 10^2$; $1.1 \times 10^4$; $3.0 \times 10^4$ | 0, $1.7 \times 10^4$; 0 |
| 0.0226 | 0.012 | $5.5 \times 10^4$; $9.5 \times 10^3$; $3.5 \times 10^4$ | 0, 0, 0 |
| 0.0574 | 0.031 | 0, 0, 0 | 0, 0, 0 |
| 0.113 | 0.061 | 0, 0, 0 | 0, 0, 0 |
| 0.226 | 0.122 | 0, 0, 0 | 0, 0, 0 |

[a]The total coating coverage averaged 20 ± 2 mg/cm$^2$;
[b]the bacterial concentration of the initial inoculum (0 h) of bacteria used to inoculate the slides was calculated to be 4.9 £ 105 § 1.1 £ 105 CFU/ml (n = 14). CFU/ml of survivors from duplicate plates The results, shown in Table 14, after 24 h confirmed the results of the lantern slide set of challenges described in Examples 27 and 28. At and above 0.012% weight Ag relative to overall coating weight (at and above 0.0025 µmol Ag/cm$^2$), the number of viable bacteria was reduced by 3-logs. The results after 12 h exposure (Table 14) showed that complete killing of the *E. coli* appeared to be obtained with levels above 0.031% weight Ag relative to overall coating weight (at and above 0.00597 µmol Ag/cm$^2$). These more muted results, in comparison with 24 h exposure results, appeared consistent with an exposure effect.

Example 32

Surviving *P. Aeruginosa* on Silver Surfactant (AgAOT) Polymer Coated Microscope Slides At each time point (0 hours, 12 hours, and 24 hours), 25 mL of sterile PBS was pipetted into the Petri dish completely submerging the glass slide coated with the antimicrobial polymer. A sterile plastic inoculating loop was used to release any viable bacteria remaining on the surface of the coating, and to mix the contents of the Petri dish. Samples from this bacterial suspension were serially diluted in PBS, plated onto TSA plates, and incubated at 37° C. for at least 24 hours.

Plates containing between 30 and 300 isolated colonies were counted and used to calculate concentrations (CFU/mL) of surviving bacteria. Results for slides used to challenge *P. aeruginosa* in triplicate are illustrated in Table 15.

TABLE 15

Challenge results for AgAOT doped polyurethane coatings exposed to *P. aeruginosa* for 12 and 24 h on microscope slide coatings[b].

| [a]% AgAOT substituted for NaAOT in Coating | % weight w/w Ag in Coating | CFU/mL of *E. coli* at 12 hours[a] | CFU/mL of *E. coli* at 24 hours |
|---|---|---|---|
| 0 | 0 | $5.5 \times 10^4$; $3.3 \times 10^5$; $1.0 \times 10^5$ | $5.0 \times 10^4$; $3.2 \times 10^5$; $2.2 \times 10^5$ |
| 0.00230 | 0.0012 | $3.0 \times 10^4$; $9.5 \times 10^5$; $2.6 \times 10^4$ | 0, 0, 0 |
| 0.00574 | 0.0031 | $1.1 \times 10^4$; $1.2 \times 10^5$; $3.3 \times 10^4$ | 0; 0; $7.5 \times 10^2$ |
| 0.0113 | 0.0061 | $4.8 \times 10^3$; $2.5 \times 10^2$; $6.3 \times 10^3$ | 0, 0, 0 |
| 0.0226 | 0.012 | $1.5 \times 10^3$; $1.5 \times 10^3$; $3.8 \times 10^3$ | $6.3 \times 10^3$; 0; $5.0 \times 10^2$ |
| 0.0574 | 0.031 | 0, 0, 0 | 0, 0, 0 |
| 0.113 | 0.061 | 0, 0, 0 | 0, 0, 0 |
| 0.226 | 0.122 | 0, 0, 0 | 0, 0, 0 |

[a]The total coating coverage averaged $20 \pm 2$ mg/cm$^2$;
[b]the bacterial concentration of the initial inoculum (0 h) of bacteria used to inoculate the slides was calculated to be $4.9 £ 105 § 1.1 £ 105$ CFU/ml (n = 14). CFU/ml of survivors from duplicate plates.

Similar to *E. coli*, the smallest substitutional level examined at 24 h exposure, 0.0012% weight Ag relative to overall coating weight (less than 0.0031 μmol Ag/cm$^2$) appears effective at killing the *P. aeruginosa*, as do all the higher challenge levels. However, the levels of 0.0031 and 0.012% (% weight Ag relative to coating weight) did not result in complete eradication in each challenge, although the assayed levels of CFU/ml in these cases were not statistically significantly different than zero. Resolution of the quantitative efficacy of this silver delivery approach for *P. aeruginosa* may await more protracted testing, but the level of 0.03 1% weight Ag relative to coating weight (0.006 μmol Ag/cm$^2$) and above appear to kill all of the *P. aeruginosa* at both 12 and 24 h exposure.

These results demonstrate that delivery of silver ion by silver bis[2-ethylhexyl]sulfosuccinate was effective as a bactericide at very low levels of bacterial exposure. Silver bis[2-ethylhexyl]sulfosuccinate was effective against both bacterial strains at overall levels of 0.06% (% weight silver relative to coating weight) with 12 hours of exposure and at 0.006% (% weight silver relative to coating weight) with 24 hours of exposure.

Example 33

*E. coli* Challenged by Silver Surfactants in Commercial Alkyd Paint

A can of commercially available alkyd resin paint (Glidden Ultrahide Oil Alkyd Semigloss white, GL-3517-0100 white, ICI Paints, Cleveland, Ohio, USA) is purchased at a paint store and used to prepare series of coated microscope slides after adding various amounts of our silver bis(2-ethylhexyl) sulfosuccinate (AgAOT) described in Example 2, silver linearalkanebenzene sulfonate (AgLABS) described in Example 4, and silver dodecyl lsulfate (AgDS) described in Example 3. Xylene/methanol (5:1 by weight) is used to dissolve the silver surfactants to facilitate homogeneously mixing with the alkyd resin composition.

TABLE 16

Challenges of *E. coli* by alkyd resin paint coating containing silver anionic surfactants; 24 h contact time.

| Weight % Ag in Coating | AgAOT | AgLABS | AgDS |
|---|---|---|---|
| 0 | + | + | + |
| 0.12 | − | − | − |
| 0.06 | − | − | − |
| 0.03 | − | − | − |
| 0.012 | − | + | + |
| 0.006 | P | + | + |
| 0.003 | + | + | + |
| 0.0012 | + | + | + |

The coatings are challenged by *E. coli* as described in Example 12, and the results of surviving bacteria are summarized in Table 16 for 24 h contact time. A minus sign (−) denotes no growth, a plus sign (+) denotes confluent growth, and a capital P (P) denotes particle growth. It appears that all three silver surfactants of the present invention are effective at preventing any growth at the 0.03 % w/w silver level. The AgAOT appears also effective at the lower level of 0.012% w/w, and partially effective at the even lower level of 0.006% w/w.

Example 34

*E. coli* Challenged by Silver Surfactants in Commercial Acrylic Paint

A can of commercially available solvent borne acrylic resin paint (PPG Bellstar Acrylic Enamel, DAR400 White; Pittsburgh Plate and Glass, Pittsburgh, Pa.) is purchased at a paint store and used to prepare series of coated microscope slides after adding various amounts of our silver bis(2-ethylhexyl)sulfosuccinate (AgAOT) described in Example 32. Xylene/methanol (5:1 by weight) is used to dissolve the silver surfactants to facilitate homogeneously mixing with the acrylic resin composition.

TABLE 17

Challenges of *E. coli* by commercial solvent borne acrylate paint coating containing silver anionic surfactants; 24 h contact time.

| Weight % Ag in Coating | AgAOT | AgLABS | AgDS |
|---|---|---|---|
| 0 | + | + | + |
| 0.12 | − | − | − |
| 0.06 | − | − | − |
| 0.03 | P | P | − |
| 0.012 | + | + | + |
| 0.006 | + | + | + |
| 0.003 | + | + | + |
| 0.0012 | + | + | + |

The coatings are used to challenge *E. coli* as described in Example 12, and the results of surviving bacteria are summarized in Table 17 after 24 h contact time. A minus sign (−) denotes no growth, a plus sign (+) denotes confluent growth, and a capital P (P) denotes particle growth. It appears all three silver surfactants of the present invention are effective at preventing any growth at the 0.06 % w/w silver level. The AgAOT and AgLABS appear partially effective at the 0.03 % Ag w/w level, and AgDS appears completely effective at this lower level. It appears the most effective silver surfactant to use in a given formulation depends on the details of the resin or binder-containing formulation and the properties of the anionic surfactant used to form the silver anionic surfactant of the present invention. Such optimization may be done by straightforward experimentation by one of ordinary skill in the art.

Example 35

S. aureus Challenged by Silver Surfactants in Laboratory Acrylic Paint

A laboratory experimental solvent based acrylic paint is formulated and then used to challenge S. aureus by adding various levels of the invention silver anionic surfactants as described in Example 33. A binder is made by solution polymerization of butyl acrylate (25% w/w), methylmethacrylate (73.5% w/w), and methacrylic acid (1.5% w/w) in amylacetate using thermal initiation. This solution polymer is then used to make a 60% solids clearcoat binder in xylene/methanol (5:1 by weight). The silver anionic surfactants are dissolved in this same xylene/methanol mixture prior to addition to the clearcoat.

TABLE 18

Challenges of E. coli by laboratory solvent borne acrylate clearcoat containing silver anionic surfactants; 24 h contact time.

| Weight % Ag in Coating | AgAOT | AgLABS | AgDS |
| --- | --- | --- | --- |
| 0 | + | + | + |
| 0.12 | − | − | − |
| 0.06 | − | − | − |
| 0.03 | − | − | − |
| 0.012 | − | P | − |
| 0.006 | − | P | − |
| 0.003 | − | − | − |
| 0.0012 | P | − | − |

The coatings are used to challenge S. aureus as described in Example 12, and the results of surviving bacteria are summarized in Table 18 after 24 h contact time. It appears all three silver surfactants of the present invention are very effective at preventing any growth down to the 0.0012% w/w silver level, with some exceptions for partial growth observed at this lowest level for AgAOT and some partial growth at 0.012 and 0.006% Ag w/w for AgLABS.

Example 36

E. coli Challenged by Silver Surfactants in Laboratory Acrylic Paint

The same laboratory experimental solvent based acrylic paint described in Example 34 is used to challenge E. coli by adding various levels of the invention silver anionic surfactants as described in Example 34.

TABLE 19

Challenges of E. coli by laboratory solvent borne acrylate paint coating containing silver anionic surfactants; 24 h contact time.

| Weight % Ag in Coating | AgAOT | AgLABS | AgDS |
| --- | --- | --- | --- |
| 0 | + | + | + |
| 0.12 | − | − | − |
| 0.06 | − | − | − |
| 0.03 | + | P | − |
| 0.012 | + | + | P |

TABLE 19-continued

Challenges of E. coli by laboratory solvent borne acrylate paint coating containing silver anionic surfactants; 24 h contact time.

| Weight % Ag in Coating | AgAOT | AgLABS | AgDS |
| --- | --- | --- | --- |
| 0.006 | + | + | + |
| 0.003 | + | + | + |
| 0.0012 | + | + | + |

The challenges to E. coli are done as described in Example 12, and the results of surviving bacteria are summarized in Table 19 after 24 h contact time. It appears all three silver surfactants of the present invention are very effective at preventing any growth down to the 0.06% w/w silver level. AgLABS has some inhibitory effects at the 0.03% level, since only partial growth is observed, and AgDS completely inhibits growth at this 0.03% level, and partially inhibits at the lower 0.012% level.

Example 37

E. coli Challenged by Silver Surfactants in Commercial 2K Epoxy Paint

A commercially available 2K epoxy resin paint is obtained from a local paint store (Sherwin Williams High Solids Epoxy Tile Clad HS; Part A B62WC11; Part B B60VZ75, The Sherwin Williams Company) and the same silver anionic surfactants described in Example 35 are used to prepare test coatings on microscope slides containing various levels of silver ion. These surfactants are dissolved in xylene/methanol (5:1 by weight) to facilitate their quantitative addition to the coating mixture.

TABLE 20

Challenges of E. coli by commercial s2K epoxy paint coating containing silver anionic surfactants; 24 h contact time.

| Weight % Ag in Coating | AgAOT | AgLABS | AgDS |
| --- | --- | --- | --- |
| 0 | + | + | + |
| 0.12 | − | − | − |
| 0.06 | − | − | − |
| 0.03 | + | − | − |
| 0.012 | + | + | P |
| 0.006 | + | + | + |
| 0.003 | + | + | + |
| 0.0012 | + | + | + |

The coatings are used to challenge E. coli as described in Example 12, and the results of surviving bacteria are summarized in Table 20 after 24 h contact time. It appears that the AgAOT is effective at complete inhibition of growth at the 0.06% w/w silver level. The AgLABS and AgDS provide complete inhibition at the lower 0.03% w/w silver level, and the AgDS is partially effective at the lower 0.012% w/w silver level.

Example 38

Polyurethane Composition with Silver bis(2-ethylhexyl)sulfosuccinate

Compositions of polyurethane suitable for forming Foley catheters based on tolyldiisocyange (TDI) and dihydroxy polyproyleneglycol (PPG) are prepared by heating the TDI and PPG in the absence of air at 90° C. overnight in the present of dibutyltin diacetate as catalyst and doped with 0-3% by weight silver ion by incorporation of AgAOT into the composition during late stages of the synthesis. PU formulated at a TDI:PPG mole ratio of 1.5:1 are post treated with water. The AgAOT is dissolved in xylene when incorporated into the polymer reaction mixture.

Example 39

Silver Surfactant Containing PU Composition Used to Challenge *E. coli* and *S. aureus*

Compositions of polyurethane (PU) containing 0, 0.01, 0.03, 0.1, 0.3, 1.0, and 3.0% w/w silver ion from AgAOT are cut into 1"×3" slabs and used to challenge both *E. coli* and *S. aureus* as described in Example 12. The duplicate challenge results of surviving bacteria are summarized in Table 21. The AgAOT incorporated into the PU appears equally effective against both bacteria and provides complete inhibition at 0.30% w/w silver.

TABLE 21

Challenges of *E. coli* and *S. aureus* by PU containing AgAOT; 24 h contact time.

| Weight % Ag in PU composition | E. coli | S. aureus |
|---|---|---|
| 0 | + | + |
| 0.01 | + | + |
| 0.03 | + | + |
| 0.10 | + | + |
| 0.30 | − | − |
| 1.0 | − | − |
| 3.0 | − | − |

Example 40

Exposure of Bacteria to Sodium Surfactant (Sodium bis[2-ethylhexyl]sulfosuccinate) on Agar Plates Sodium bis[2-ethylhexyl]sulfosuccinate was obtained from Fisher Scientific (Hanover, Ill., U.S.A.). Plates containing 0.5% sodium bis[2-ethylhexyl]sulfosuccinate were prepared by adding an equal volume of filter sterilized sodium bis[2-ethylhexyl]sulfosuccinate to sterile, molten Trypticase Soy Agar (TSA) that was mixed and autoclaved at a 2× concentration. This solution was then aliquoted into sterile petri dishes, approximately 25 mL per plate, and allowed to solidify. The organisms were grown in 5 mL of Trypticase Soy Broth. The sterile broth was inoculated with a single isolated colony from a stock culture and allowed to incubate in a shaking water bath at 37° C. for 8-10 hours. The estimated concentration was about $10^9$ CFU/mL. Some plates were tested with a 1:100 dilution of these cultures to arrive at an approximate concentration of $10^7$ CFU/mL. Then, 10 μL of each overnight culture was pipetted directly onto the surface of the surfactant/TSA plates, which were then allowed to incubate at 37° C. for 24 hours. Results were based on the presence or absence of bacterial growth on the surface of the agar.

Growth of the bacteria was inhibited on plates containing sodium bis[2-ethylhexyl]sulfosuccinate, but growth was sustained on plates free of sodium bis[2-ethylhexyl]sulfosuccinate. This inhibition appeared to be specific for Gram-positive bacteria, and it was not observed for Gram-negative bacteria. All Gram-negative bacteria tested, except for *Serratia marcescens*, was resistant to the presence of sodium bis[2-ethylhexyl]sulfosuccinate. All Gram-positive bacteria tested, as well as the yeast *Candida tropicalis*, was killed on agar plates containing sodium bis[2-ethylhexyl]sulfosuccinate. Results are shown in Tables 22 and 23.

TABLE 22

Survival of Gram-positive bacteria (and the yeast *Candida tropicalis*) exposed to sodium surfactant (sodium bis[2-ethylhexyl]sulfosuccinate) on agar plates.

| | *No Growth(−)/Full Growth(+) | | | |
|---|---|---|---|---|
| | TSA with 0.5% sodium bis[2-ethylhexyl]sulfosuccinate | | TSA without sodium bis[2-ethylhexyl]sulfosuccinate | |
| Gram-positive Bacteria Name | 1* | 2* | 1* | 2* |
| Staphylococcus aureus | − | − | + | + |
| Bacillus subtilis | − | − | + | + |
| Streptococcus viridans | − | − | − | + |
| Staphylococcus aureus | − | − | + | + |
| Streptococcus bovis | − | − | + | + |
| Enterococcus fecalis | − | − | + | + |
| Staphylococcus epidermidis | − | − | + | + |
| Streptococcus pneumoniae | − | − | − | − |
| Streptococcus pyogenes | − | − | + | + |
| Streptococcus agalactiae | − | − | + | + |
| Candida tropicalis | − | − | + | + |
| Bacillus subtilis | − | − | + | + |
| Micrococcus luteus | − | − | + | + |

TABLE 23

Survival of Gram-positive bacteria exposed to various sodium surfactants, with structures shown in Table 24, on agar plates.

| | | *No Growth(−)/Full Growth(+) Compound # | | | | | | | | | | | | | | | | | |
|---|---|---|---|---|---|---|---|---|---|---|---|---|---|---|---|---|---|---|---|
| | | $S_1$ | | $S_2$ | | $S_3$ | | | $S_4$ | | | $S_5$ | | | $S_6$ | | | | |
| Bacterial Name | Strain | 1 | 2 | 1 | 2 | 1 | 2 | 3 | 1 | 2 | 3 | 1 | 2 | 3 | 1 | 2 | 3 | | |
| Staphylococcus aureus | ATCC6538 | − | − | − | − | − | − | − | + | + | + | + | + | + | + | + | + | | |
| Bacillus subtilis | ATCC33 | − | − | − | − | − | − | − | − | P | + | − | − | P | + | + | − | | |
| Streptococcus viridans | EM8 | − | − | − | − | − | + | P | + | + | + | + | + | + | + | + | + | | |

TABLE 23-continued

Survival of Gram-positive bacteria exposed to various sodium surfactants, with structures shown in Table 24, on agar plates.

*No Growth(−)/Full Growth(+)

| Bacterial Name | Strain | S₁ |  | S₂ |  | S₃ |  |  | S₄ |  |  | S₅ |  |  | S₆ |  |  |
|---|---|---|---|---|---|---|---|---|---|---|---|---|---|---|---|---|---|
|  |  | 1 | 2 | 1 | 2 | 1 | 2 | 3 | 1 | 2 | 3 | 1 | 2 | 3 | 1 | 2 | 3 |
| *Staphylococcus aureus* | EM24/ATCC25923 | − | − | − | − | − | − | − | + | + | + | + | + | + | + | + | + |
| *Streptococcus bovis* | EM12 | − | − | − | − | − | − | − | − | − | − | − | − | − | − | − | − |
| *Enterococcus fecalis* | EM19 | − | − | − | − | − | P | P | + | + | + | + | + | + | + | + | + |
| *Enterococcus fecalis* | EM19 | − | − | − | − | + | + | + | + | + | + | + | + | + | + | + | + |
| *Staphylococcus epidermidis* | EM3/ATCC12228 | − | − | − | − | − | P | − | + | + | + | + | + | + | + | + | + |
| *Streptococcus pyogenes* | EM14 | − | − | − | − | − | − | − | − | − | − | − | − | − | − | − | − |
| *Streptococcus agalactiae* | EM13 | − | − | − | − | − | − | − | P | + | − | − | + | − | + | − | − |
| *Bacillus subtilis* | EM27 | − | − | − | − | − | − | P | P | P | + | − | P | + | − | + | − |
| *Micrococcus luteus* | EM17 | − | − | − | − | P | P | − | − | − | + | + | − | − | + | + | + |

TABLE 24

Chemical structures of compounds to which Gram-positive bacteria were exposed, as in Table 23.

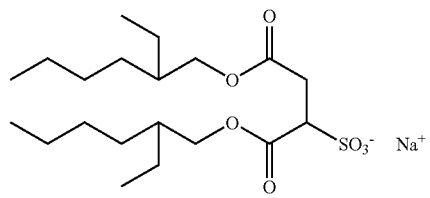

S₁

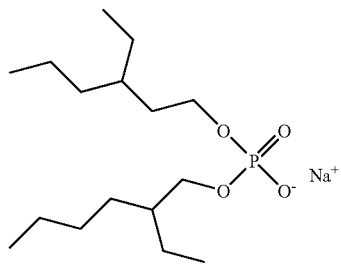

S₂

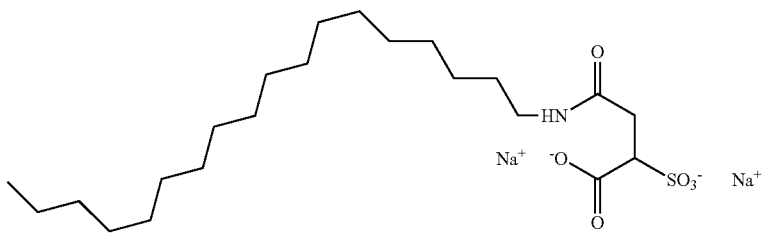

S₃

TABLE 24-continued

Chemical structures of compounds to which Gram-positive bacteria were exposed, as in Table 23.

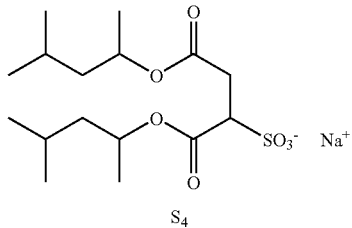

S4

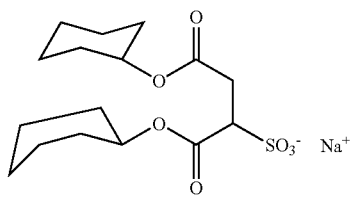

S5

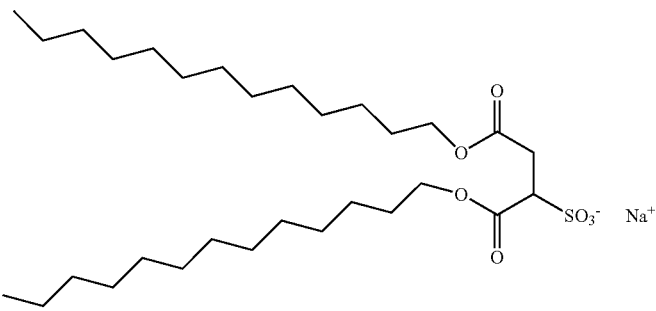

S6

Not all of the Gram-positive bacteria were eradicated equally by the surfactants evaluated as antimicrobial agents. Efficacy of the surfactants as antimicrobial agents varied with effective hydrophobicity, or C×log P, of the surfactant, where P is the calculated partition coefficient of the surfactant between 1-octanol and water, and where C is the concentration of the surfactant. Compounds 2 and 20 were effective antimicrobial agents against all Gram-positive bacteria tested. The relative ranking of hydrophobicity, and activity as antibacterial agents for Gram-positive bacteria, was the following for the compounds: 5~6<2~20<4<3.

Example 41

Exposure of Bacteria to Sodium Surfactant Polymer Coated Slides

Microscope slides with polymeric coatings containing the sodium surfactant of sodium bis[2-ethylhexyl]sulfosuccinate were prepared according to the following, except all slides contained 30% (by weight) sodium bis[2-ethylhexyl]sulfosuccinate and no silver bis[2-ethylhexyl]sulfosuccinate: Glass lantern slides (2×3 inches, Fisher Scientific, Hanover, Ill., U.S.A.) and microscope slides (1×3 inches, Fisher Scientific, Hanover, Ill., U.S.A.) were sterilized to rid them of any contaminating microorganisms by exposing the slides to a germicidal UV lamp in a Nuaire Model NU-455-600 Class II Type A/B3 laminar flow hood (2 minute-exposure on each side at room temperature). The glass slides were then washed with acetone and water.

Polyurethane coatings were formed on the glass slides in situ using microemulsion polymerization as described in Texter et al. *supra*. The microemulsions were formulated with equivalent weights of the immiscible step-polymerization monomers propylene glycol (PG) and isophorone diisocyanate (IPDI), along with sodium bis[2-ethylhexyl]sulfosuccinate (as described in Example 1) at 30% (% weight relative to weight of all three components). Dibutyltin dilaurate (DBTD) was used as a catalyst to drive the step polymerization, and it was added to 0.1% of the total composition weight. Coatings of approximately 150 μm thickness and 5 cm width were made on glass slides using a drawdown bar. The coatings were stored for at least ten days a room temperature before being subjected to challenge testing. These sodium bis[2-ethylhexyl]sulfosuccinate coatings were used as control coatings in the subsequent challenges. Silver bis[2-ethylhexyl] sulfosuccinate (prepared as described in Example 1) was substituted for sodium bis[2-ethylhexyl]sulfosuccinate on a weight basis (of the total composition) from 10% to 0.01% by weight, during the microemulsion formation stage prior to coating, to produce test coatings.

Sodium bis[2-ethylhexyl]sulfosuccinate killed all of the *B. subtilis* and *S. aureus* after 12 and 24 hours of exposure (Table 25).

TABLE 25

Survival of bacteria exposed to sodium surfactant (sodium bis[2-ethylhexyl]sulfosuccinate) polyurethane coated microscope slides. Two data sets are shown.

| Exposure (hours) | CFU/mL B. subtilis | CFU/mL S. aureus |
|---|---|---|
| 0 | $3.6 \times 10^4$ | $2.0 \times 10^5$ |
|   | $1.6 \times 10^4$ | $5.1 \times 10^5$ |
| 12 | 0 | 0 |
|   | 0 | 0 |
| 24 | 0 | 0 |
|   | 0 | 0 |

While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A bactericidal composition comprising:
   (a) a silver ion monodentate ligand complex, the ligand being an anionic surfactant comprising a surfactant anion comprising two surfactant tail groups and promoting reverse micelle formation; and
   (b) a polymeric binder;
   wherein the silver ion monodentate ligand complex is homogeneously distributed throughout the polymeric binder.

2. A method for making a bactericidal coating comprising:
   (a) providing the bactericidal composition according to claim 1; and
   (b) applying the bactericidal composition to a substrate to produce a silver-containing bactericidal coating.

3. The composition of claim 1, wherein the anionic surfactant comprises a sulfosuccinate diester.

4. A method for making a bactericidal composition comprising:
   (a) dissolving a silver ion monodentate ligand complex in a suitable solvent to produce a silver ion-containing solution, ligand being an anionic surfactant; and
   (b) mixing said solution with a composition comprising a polymeric binder to produce the bactericidal composition of claim 1.

5. The composition of claim 1, wherein the silver ion monodentate ligand complex comprises bis(2-ethylhexyl)sulfosuccinate.

6. The composition of claim 1, wherein the silver ion is present in the composition at a level at or above 0.03 wt. % relative to the polymeric binder.

7. The composition of claim 1, further comprising:
   (c) a solvent;
   wherein:
   (i) the silver ion monodentate ligand complex is dissolved in the solvent to form a silver ion-containing solution;
   (ii) the polymeric binder is selected from the group consisting of polymers and polymer precursor monomers; and
   (iii) the polymeric binder is mixed in the silver ion-containing solution.

8. The composition of claim 1, further comprising:
   (c) a solvent;
   wherein:
   (i) the silver ion monodentate ligand complex is dissolved in the solvent to form a silver ion-containing solution;
   (ii) the polymeric binder comprises a polymer; and
   (iii) the polymeric binder is mixed in the silver ion-containing solution.

9. The composition of claim 1, further comprising:
   (c) a solvent;
   wherein:
   (i) the silver ion monodentate ligand complex is dissolved in the solvent to form a silver ion-containing solution;
   (ii) the polymeric binder comprises polymer precursor monomers; and
   (iii) the polymeric binder is mixed in the silver ion-containing solution.

10. The composition of claim 9, further comprising crosslinking agents for the polymer precursor monomers.

11. The composition of claim 1, wherein the silver ion monodentate ligand complex is solubilized in the polymeric binder.

12. An article comprising:
    (a) a substrate; and
    (b) the composition of claim 1 as a coating on the substrate.

13. The article of claim 12, wherein the substrate is a catheter.

14. The method of claim 4, further comprising:
    (c) curing the bactericidal composition.

15. The method of claim 2, wherein applying the bactericidal composition comprises coating.

16. The method of claim 2, further comprising:
    (c) curing the silver-containing bactericidal coating.

17. A bactericidal composition comprising:
    (a) a silver ion monodentate ligand complex, the ligand being an anionic surfactant comprising a surfactant anion comprising two surfactant tail groups and promoting reverse micelle formation; and
    (b) a polymeric binder.

18. The bactericidal composition of claim 17, wherein the anionic surfactant comprises a sulfosuccinate diester.

19. A bactericidal composition comprising:
    (a) a silver ion monodentate ligand complex, the ligand being an anionic polyelectrolyte; and
    (b) a polymeric binder.

20. The bactericidal composition of claim 19, wherein the polyelectrolyte comprises anionic functional groups selected from the group consisting of carboxylates, sulfates, sulfonates, and phosphates.

* * * * *